(12) United States Patent
Itoi et al.

(10) Patent No.: US 11,381,767 B2
(45) Date of Patent: Jul. 5, 2022

(54) SOLID-STATE IMAGING DEVICE HAVING ELECTRONIC COMPONENTS MOUNTED BETWEEN A MAIN SUBSTRATE AND AN IMAGING ELEMENT

(71) Applicant: Panasonic Intellectual Property Management Co., Ltd., Osaka (JP)

(72) Inventors: Kiyokazu Itoi, Osaka (JP); Takeru Tamari, Osaka (JP); Daisuke Sakurai, Osaka (JP); Shozo Ochi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 185 days.

(21) Appl. No.: 16/803,551

(22) Filed: Feb. 27, 2020

(65) Prior Publication Data

US 2020/0195867 A1    Jun. 18, 2020

Related U.S. Application Data

(63) Continuation of application No. PCT/JP2018/036629, filed on Oct. 1, 2018.

(30) Foreign Application Priority Data

Oct. 20, 2017 (JP) .............................. JP2017-203532
Jul. 2, 2018 (JP) .............................. JP2018-125684
(Continued)

(51) Int. Cl.
*H04N 5/369* (2011.01)
*H01L 27/146* (2006.01)
(Continued)

(52) U.S. Cl.
CPC ....... *H04N 5/369* (2013.01); *H01L 27/14607* (2013.01); *H01L 27/14618* (2013.01);
(Continued)

(58) Field of Classification Search
CPC .... H04N 5/369; H04N 5/2252; H04N 5/2257; H04N 5/2253; H04N 5/2251;
(Continued)

(56) References Cited

U.S. PATENT DOCUMENTS 6,567,115 B1    5/2003   Miyashita et al.
8,013,350 B2 *  9/2011   Itoi ..................... H01L 33/62
                                                          257/98
(Continued)

FOREIGN PATENT DOCUMENTS

JP    2000-199863    7/2000
JP    2001-017389    1/2001
(Continued)

OTHER PUBLICATIONS

International Search Report of PCT application No. PCT/JP2018/036629 dated Dec. 18, 2018.
(Continued)

*Primary Examiner* — Albert H Cutler
(74) *Attorney, Agent, or Firm* — Wenderoth, Lind & Ponack, L.L.P.

(57) ABSTRACT

A solid-state imaging device includes a solid-state imaging element and a substrate fixed to the solid-state imaging element by a sealing resin on a surface on an opposite side of a light receiving surface of the solid-state imaging element, an outer edge of the substrate seen from the light receiving surface side of the solid-state imaging element is positioned within an outer edge of the solid-state imaging element and an outer edge of the sealing resin seen from the light receiving surface side of the solid-state imaging element is positioned within the outer edge of the solid-state imaging element. The sealing resin includes a first sealing resin and a second sealing resin not contacting the first sealing resin to seal the components.

8 Claims, 18 Drawing Sheets

(30) Foreign Application Priority Data

Jul. 2, 2018 (JP) .............................. JP2018-125685
Jul. 3, 2018 (JP) .............................. JP2018-126476

(51) Int. Cl.
*H04N 5/225* (2006.01)
*A61B 1/04* (2006.01)
*A61B 1/05* (2006.01)
*G02B 23/24* (2006.01)

(52) U.S. Cl.
CPC ..... *H01L 27/14683* (2013.01); *H04N 5/2252* (2013.01); *H04N 5/2257* (2013.01); *A61B 1/04* (2013.01)

(58) Field of Classification Search
CPC ......... H01L 27/14607; H01L 27/14618; H01L 27/14683; A61B 1/04; A61B 1/051; G02B 23/24
See application file for complete search history.

(56) References Cited

U.S. PATENT DOCUMENTS

| | | | |
|---|---|---|---|
| 8,698,887 | B2 | 4/2014 | Makino et al. |
| 11,102,384 | B2* | 8/2021 | Wang ................... H04N 5/2252 |
| 2001/0050717 | A1* | 12/2001 | Yamada ............ H01L 27/14625 |
| | | | 348/340 |
| 2008/0211045 | A1* | 9/2008 | Ono ................... H01L 27/14685 |
| | | | 257/432 |
| 2015/0228678 | A1* | 8/2015 | Yoshida .............. H01L 27/1464 |
| | | | 600/110 |
| 2015/0312457 | A1* | 10/2015 | Kojima ................ H04N 5/2257 |
| | | | 348/76 |
| 2017/0134624 | A1* | 5/2017 | Zhang .................. H04N 5/2253 |
| 2018/0006070 | A1 | 1/2018 | Isobe |
| 2018/0041670 | A1* | 2/2018 | Fujimori ................. H01L 27/14 |

FOREIGN PATENT DOCUMENTS

| | | |
|---|---|---|
| JP | 2008-219854 | 9/2008 |
| JP | 2011-217887 | 11/2011 |
| JP | 2017-094044 | 6/2017 |
| WO | 2015/146332 | 10/2015 |
| WO | 2016/129409 | 8/2016 |

OTHER PUBLICATIONS

Extended European Search Report dated Nov. 19, 2020 in corresponding European Patent Application No. 18867857.7.

* cited by examiner

[FIG. 1]
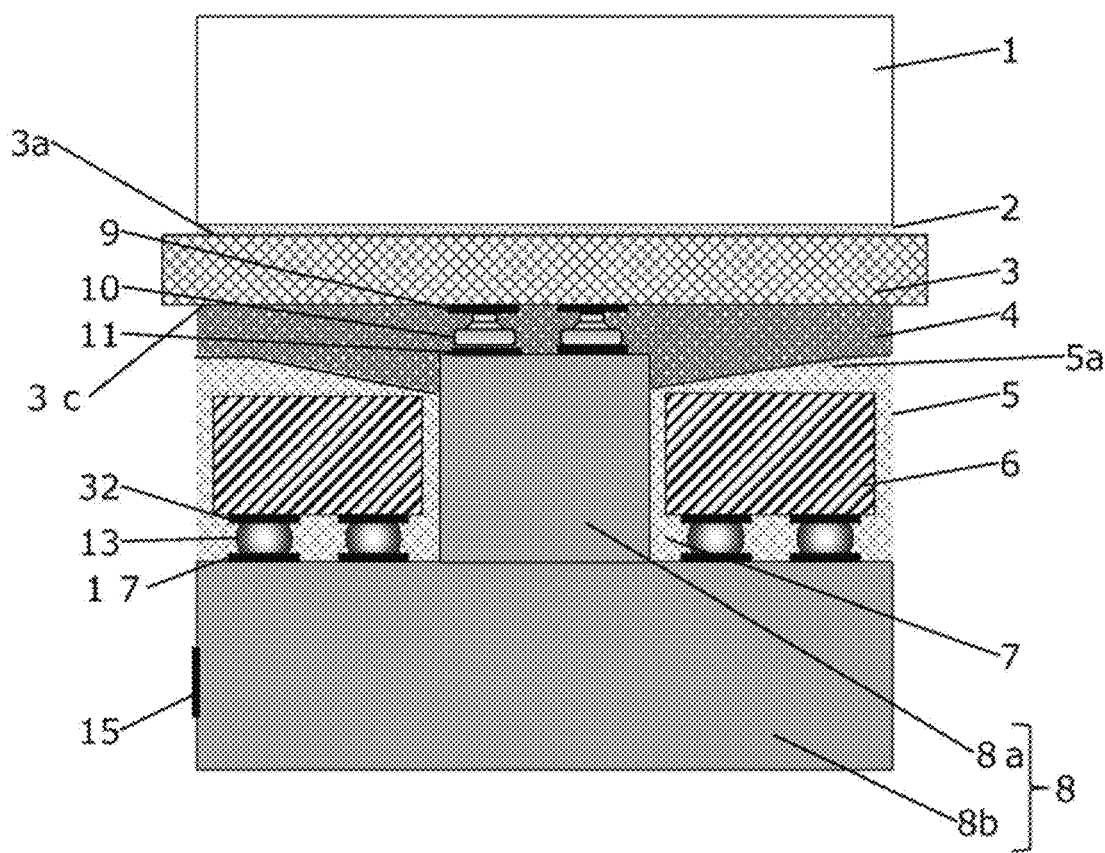

[FIG. 2]
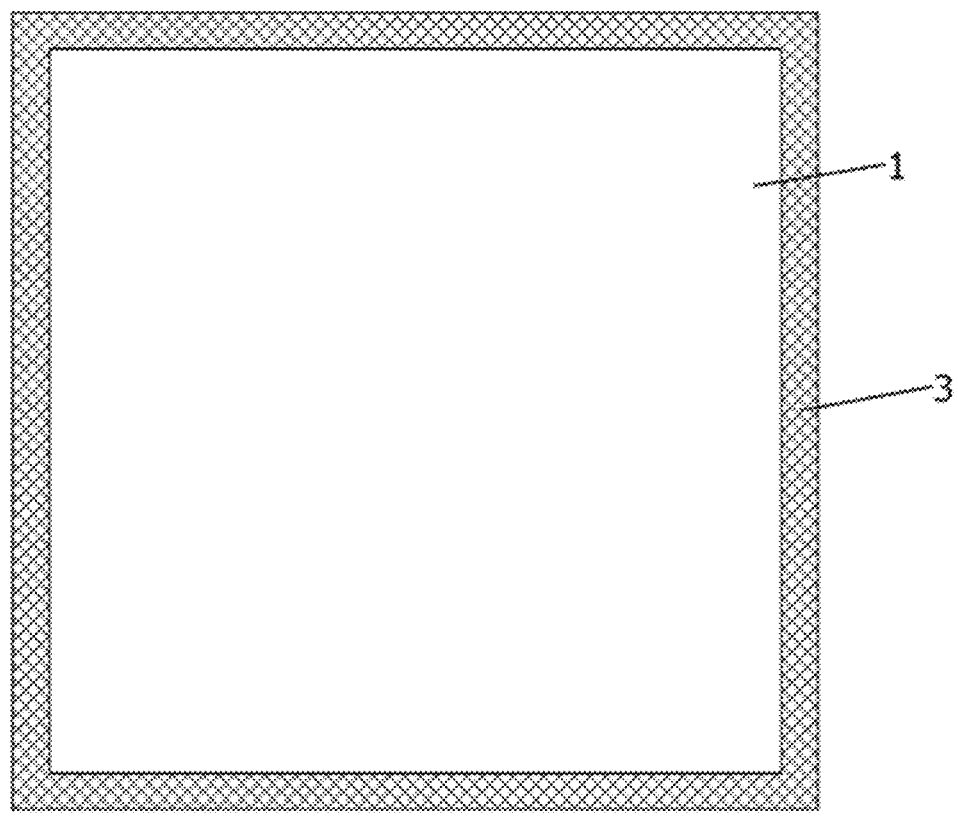

[FIG. 3]
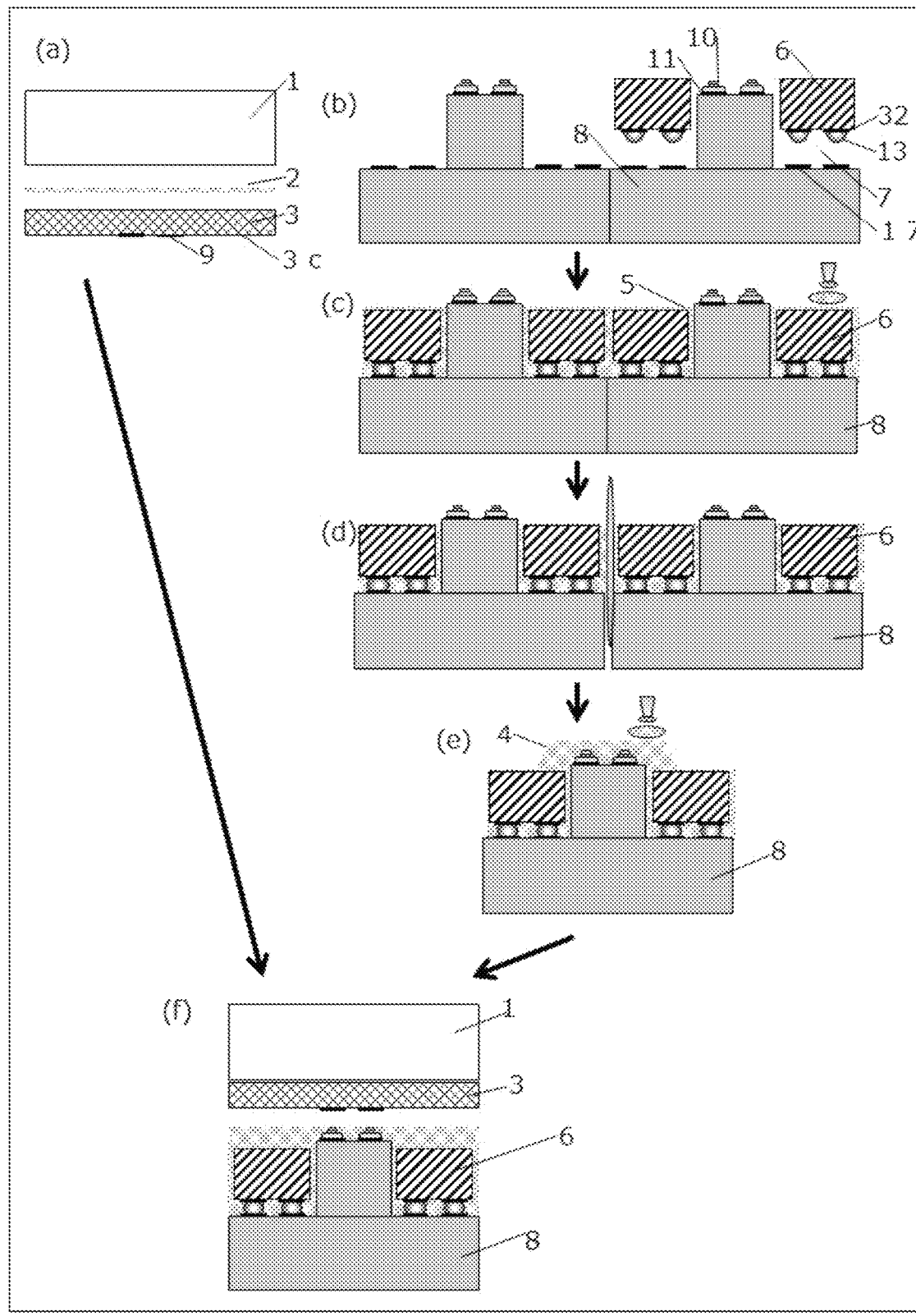

[FIG. 4]
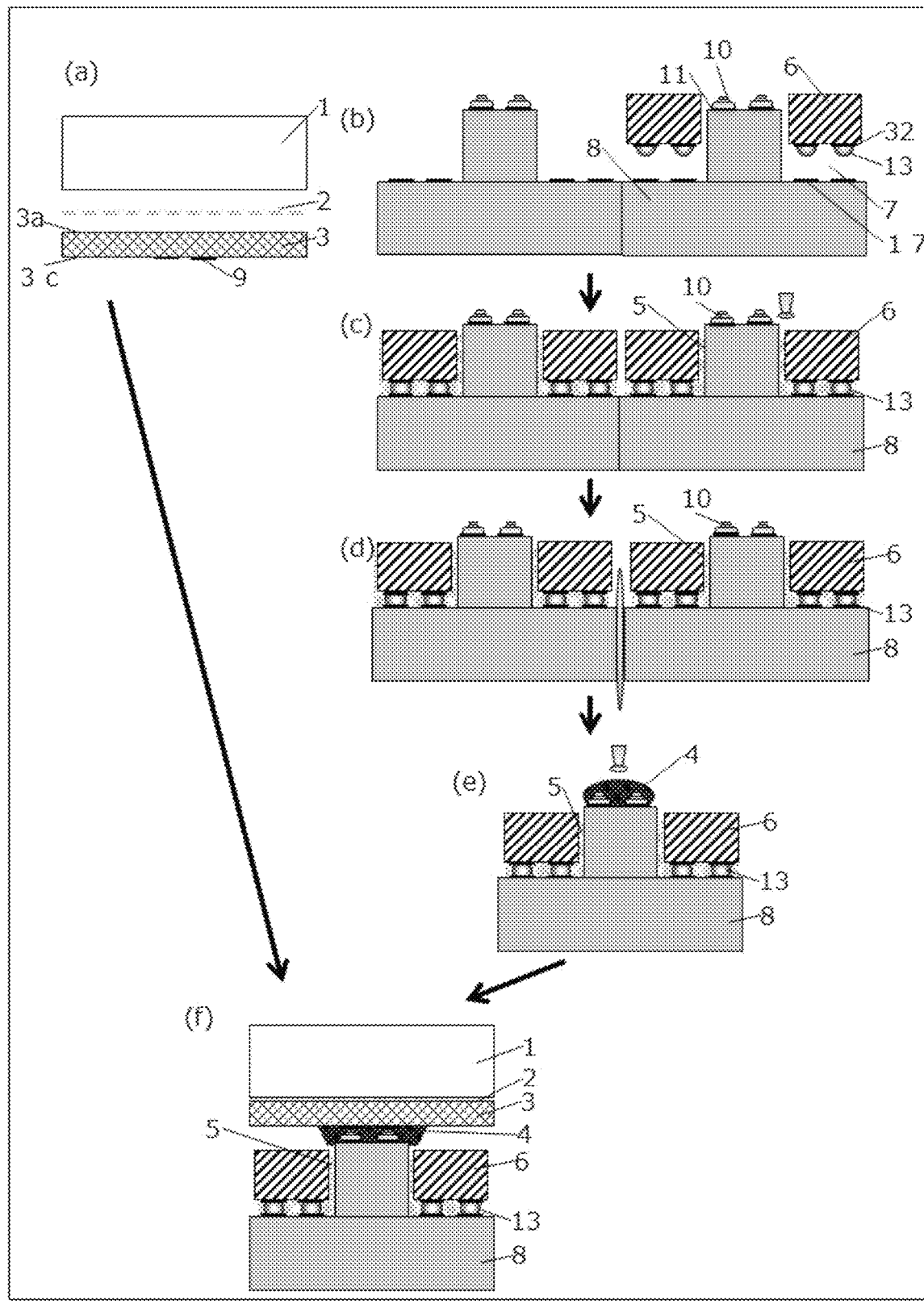

[FIG. 5]
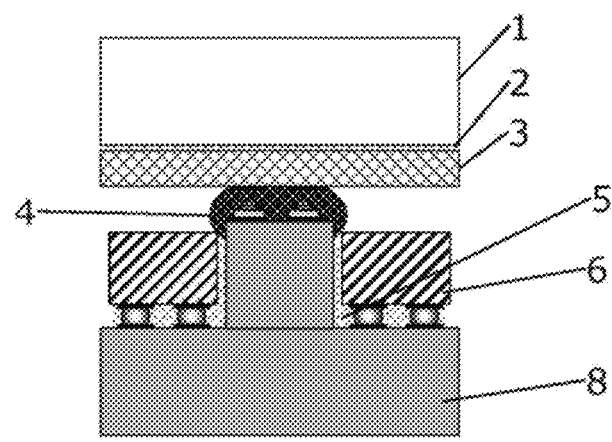
[FIG. 6]
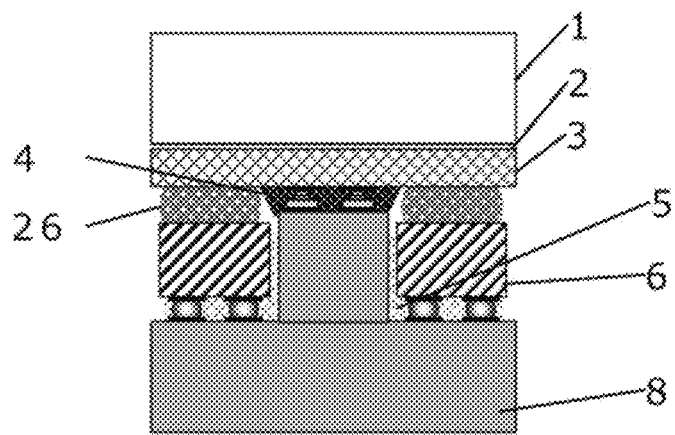

[FIG. 7]
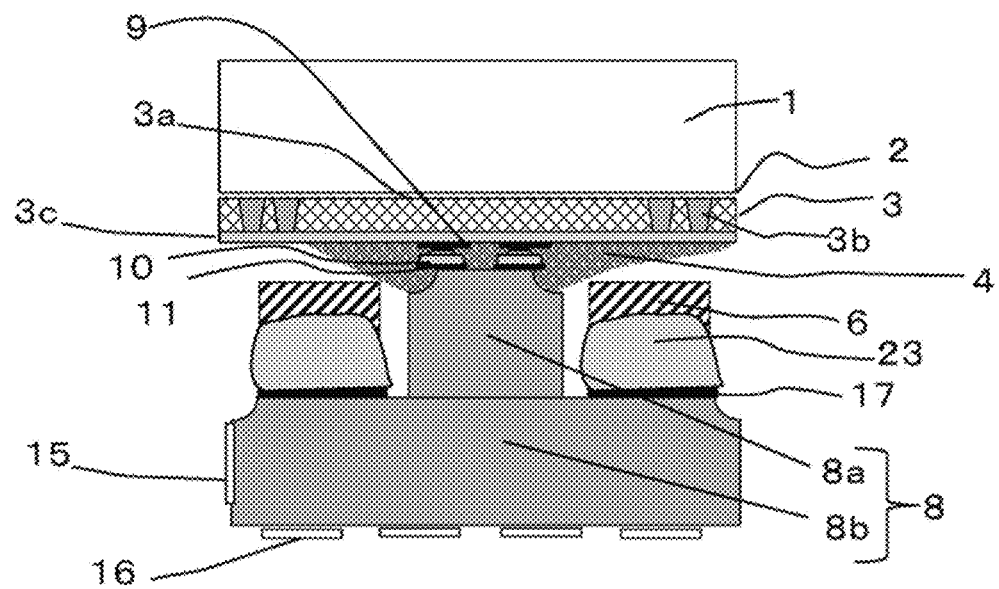
[FIG. 8]
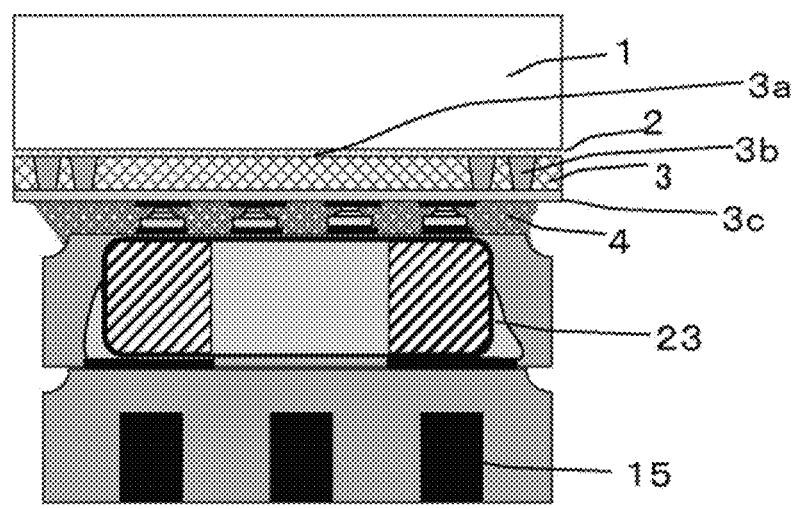

[FIG.9]
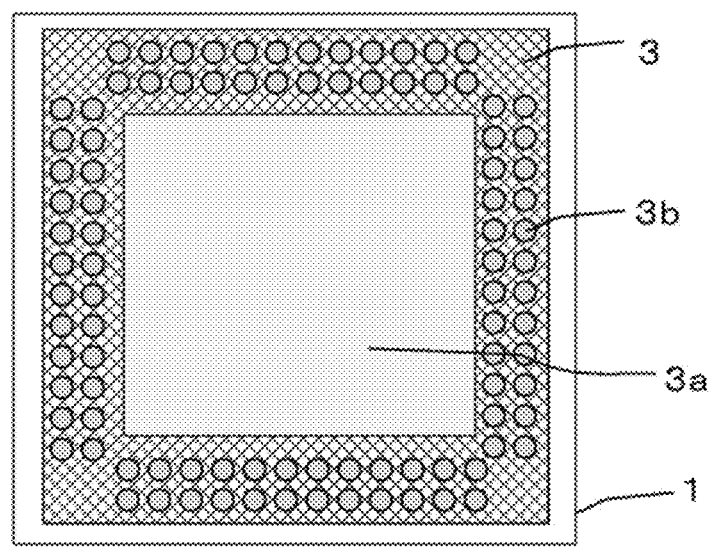

[FIG. 10]
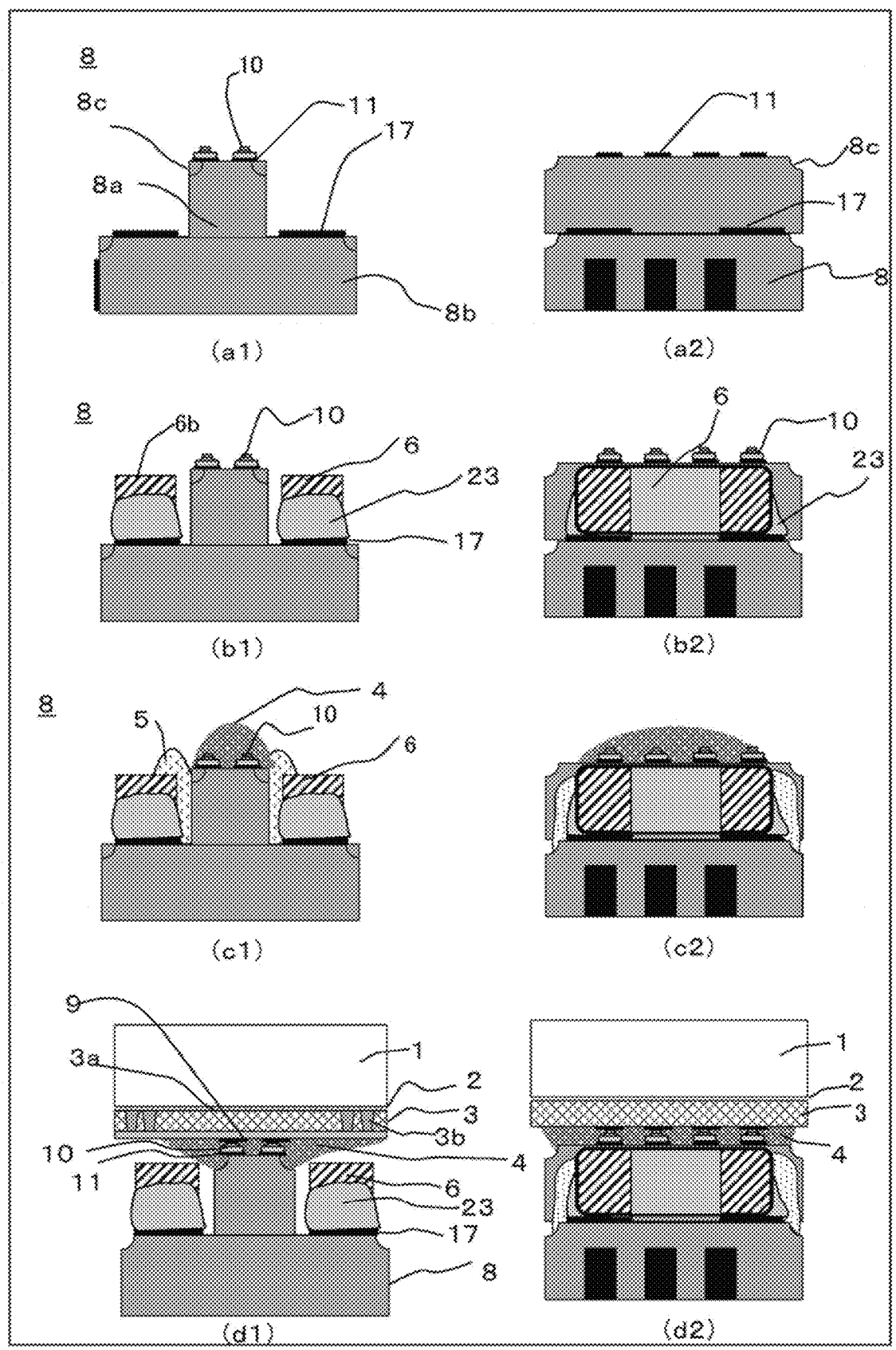

[FIG. 11]
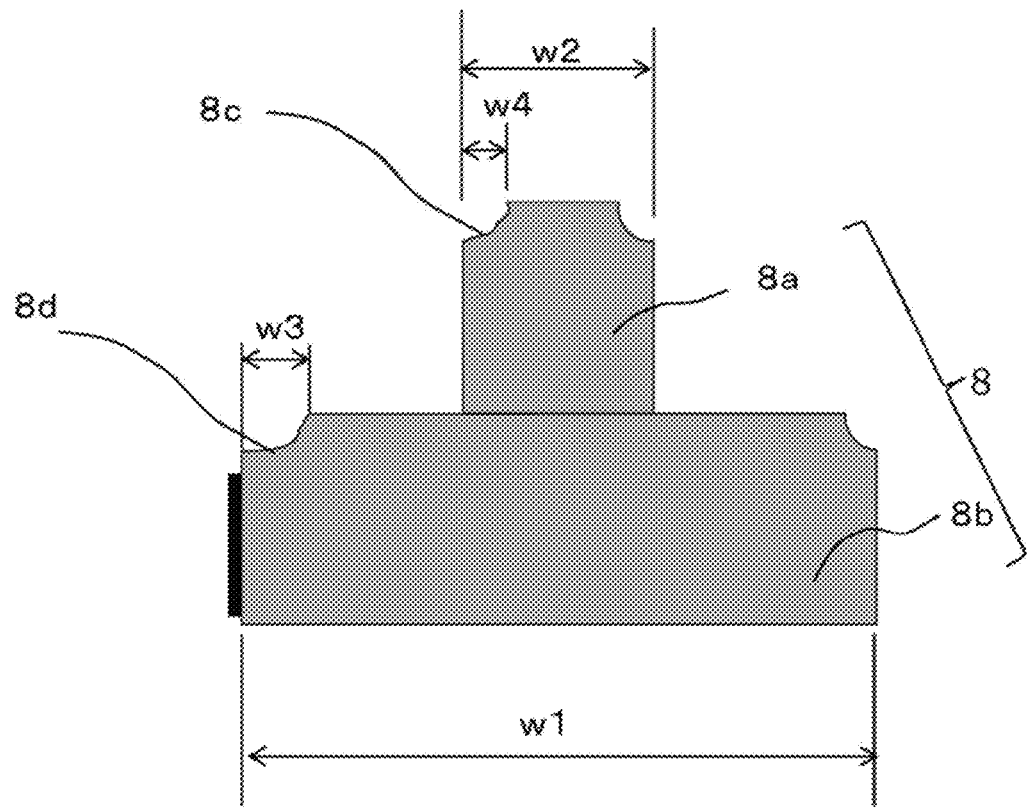
[FIG. 12]
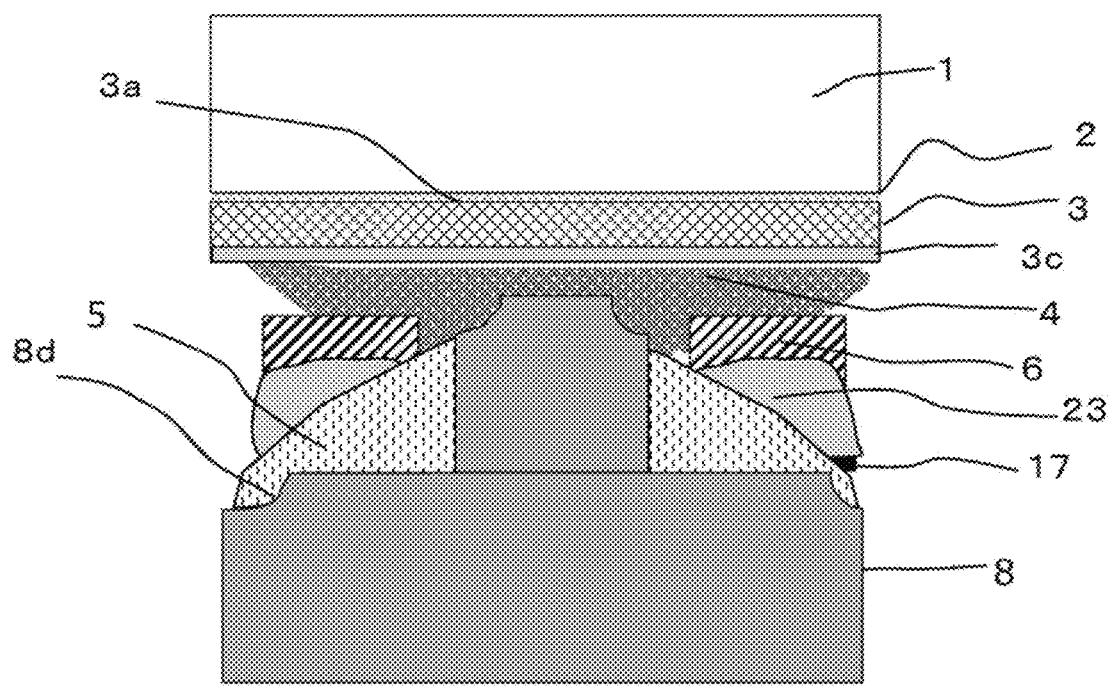

[FIG. 13]
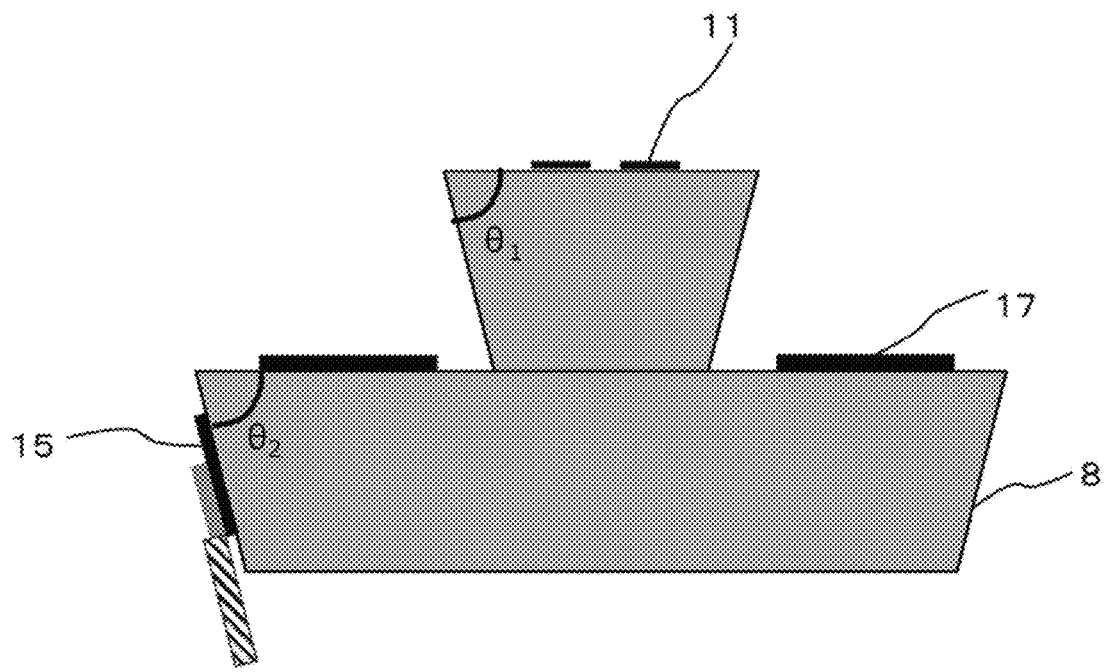
[FIG. 14]
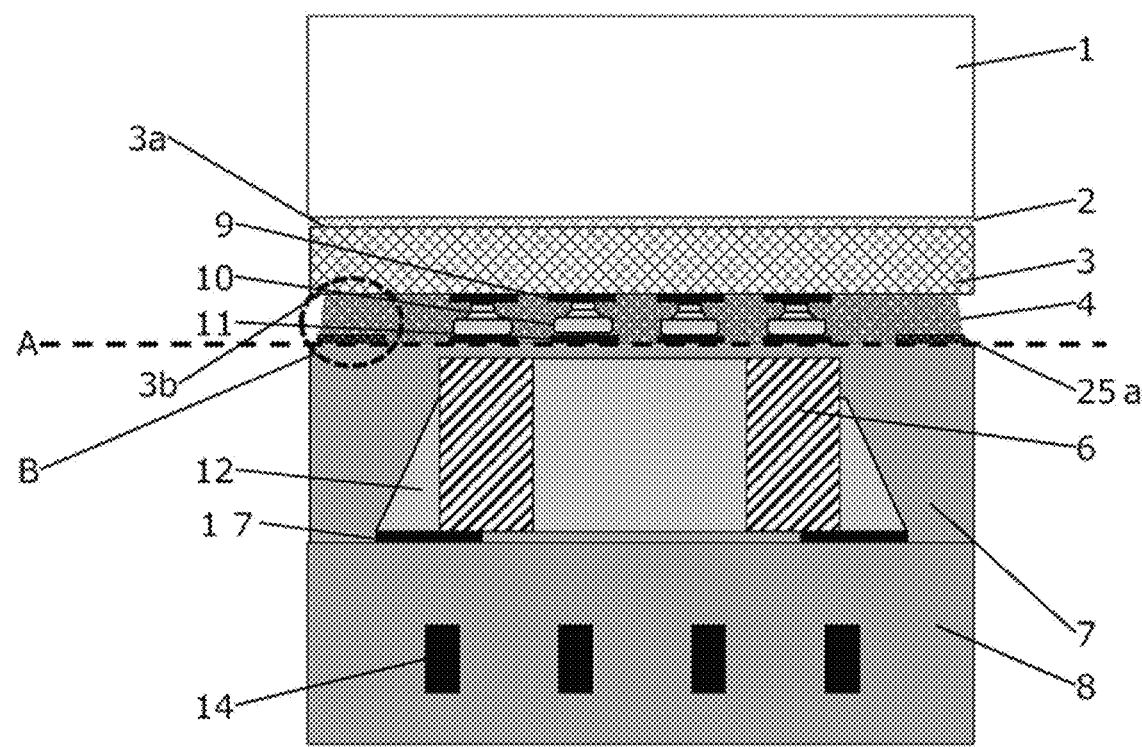

[FIG. 15]
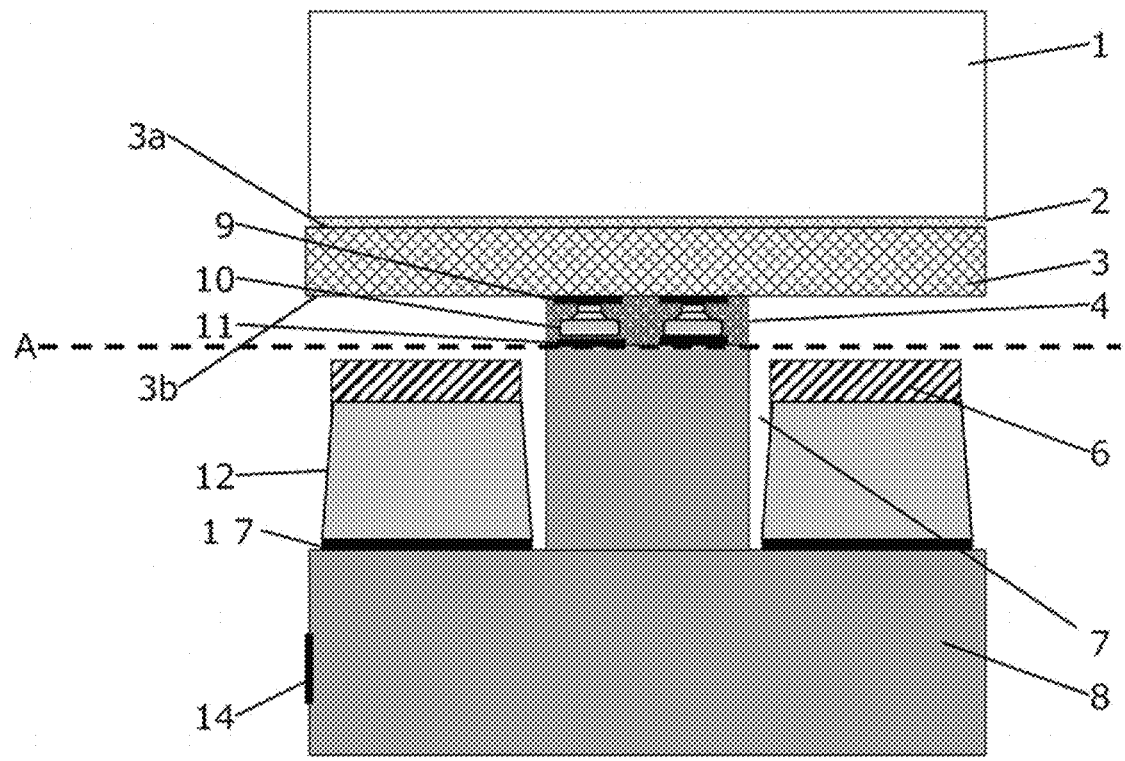
[FIG. 16]
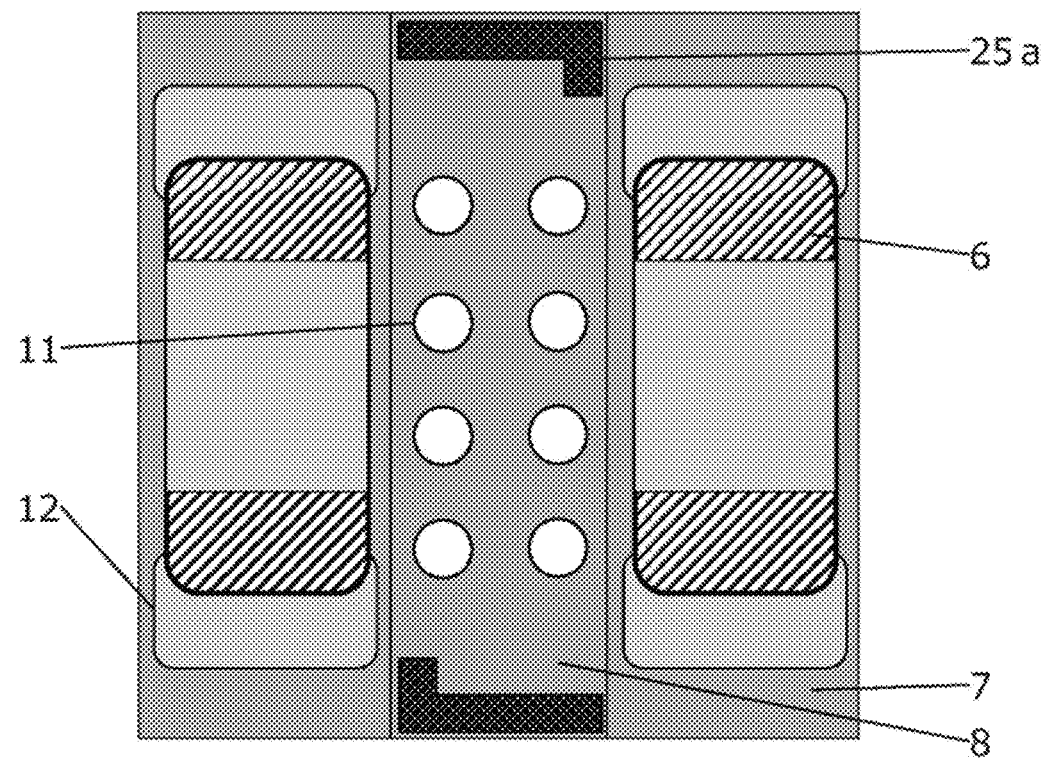

[FIG. 17]
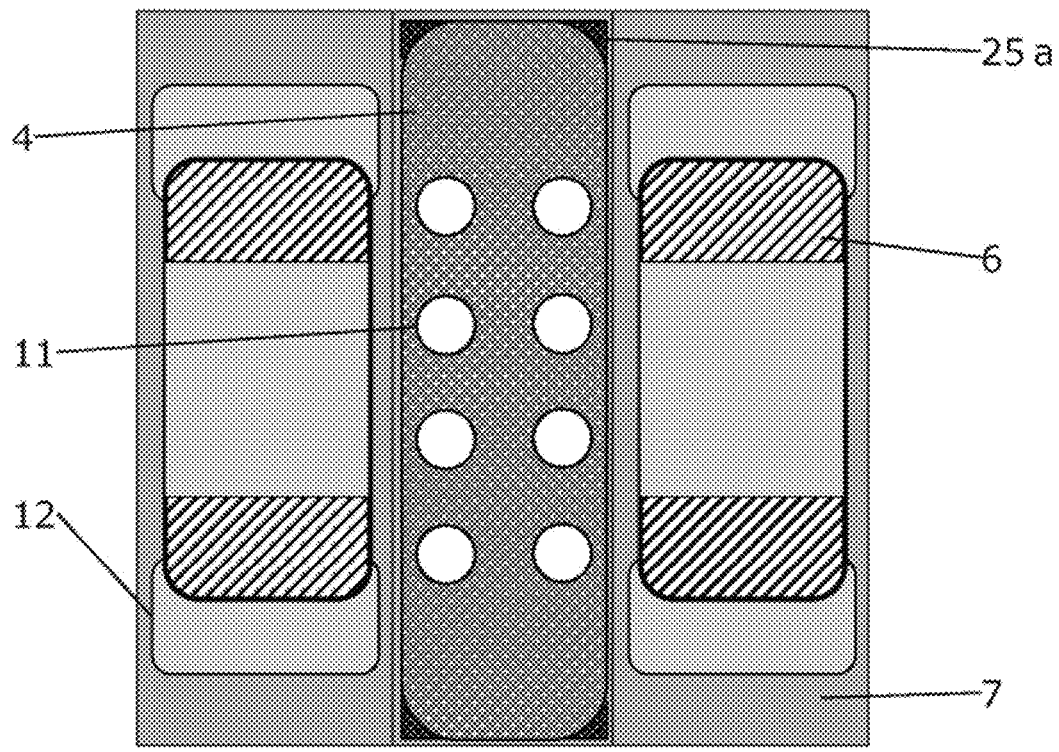
[FIG. 18]
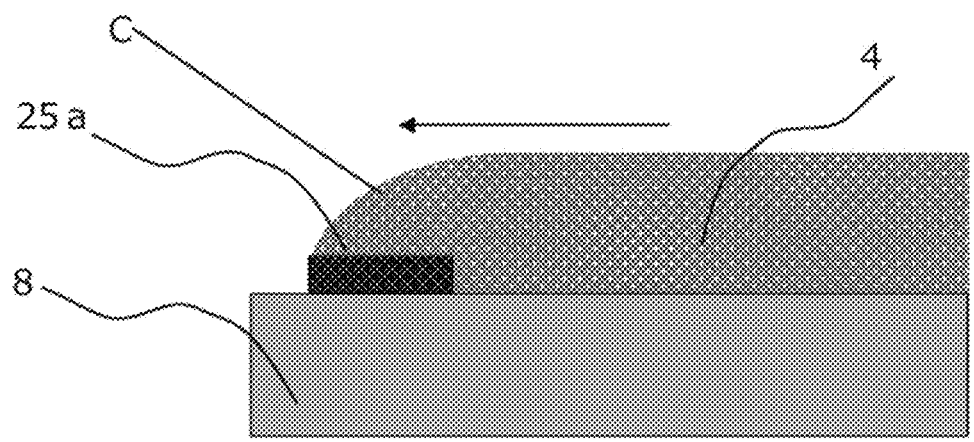

[FIG. 19]
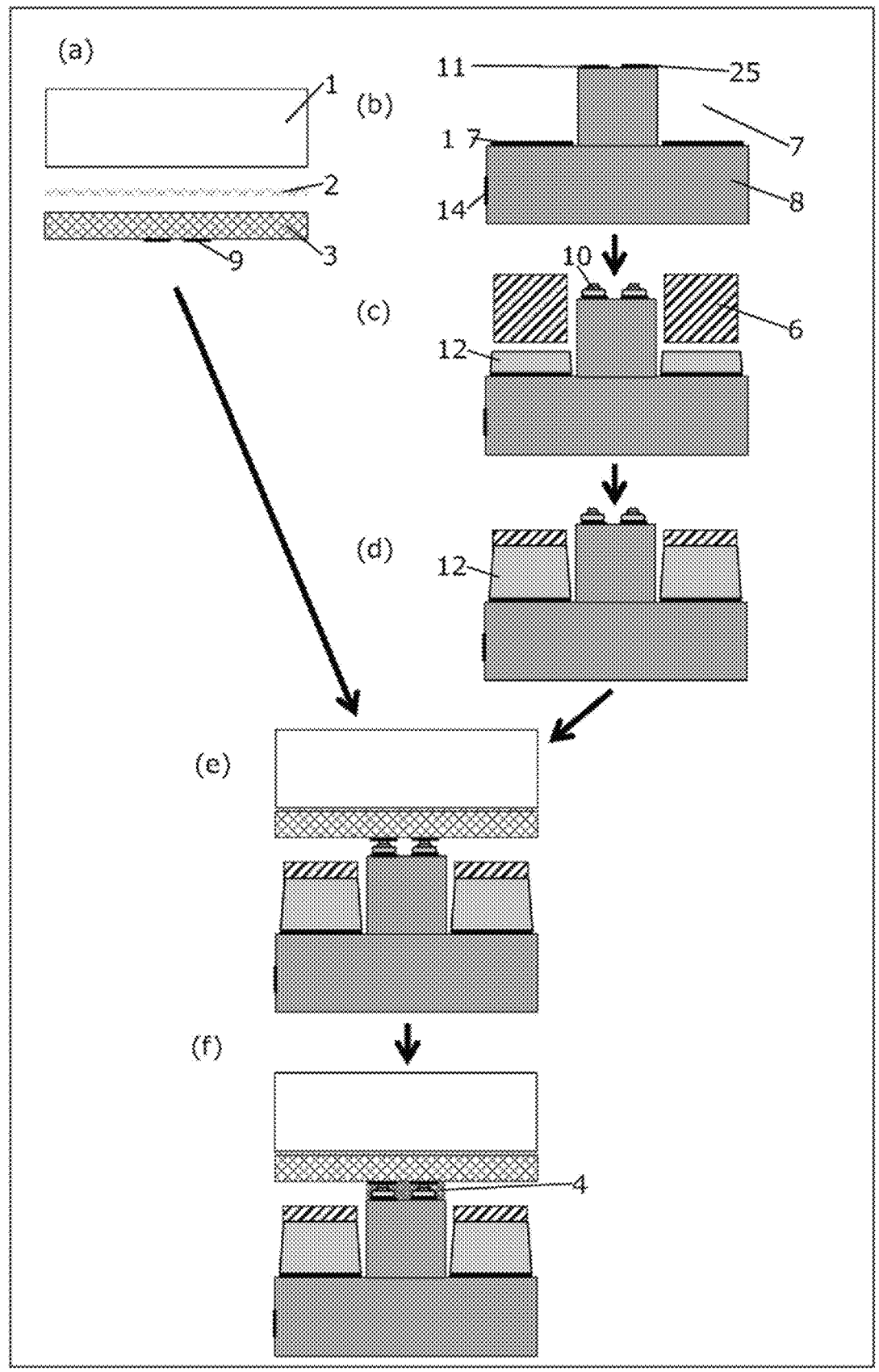

[FIG. 20]
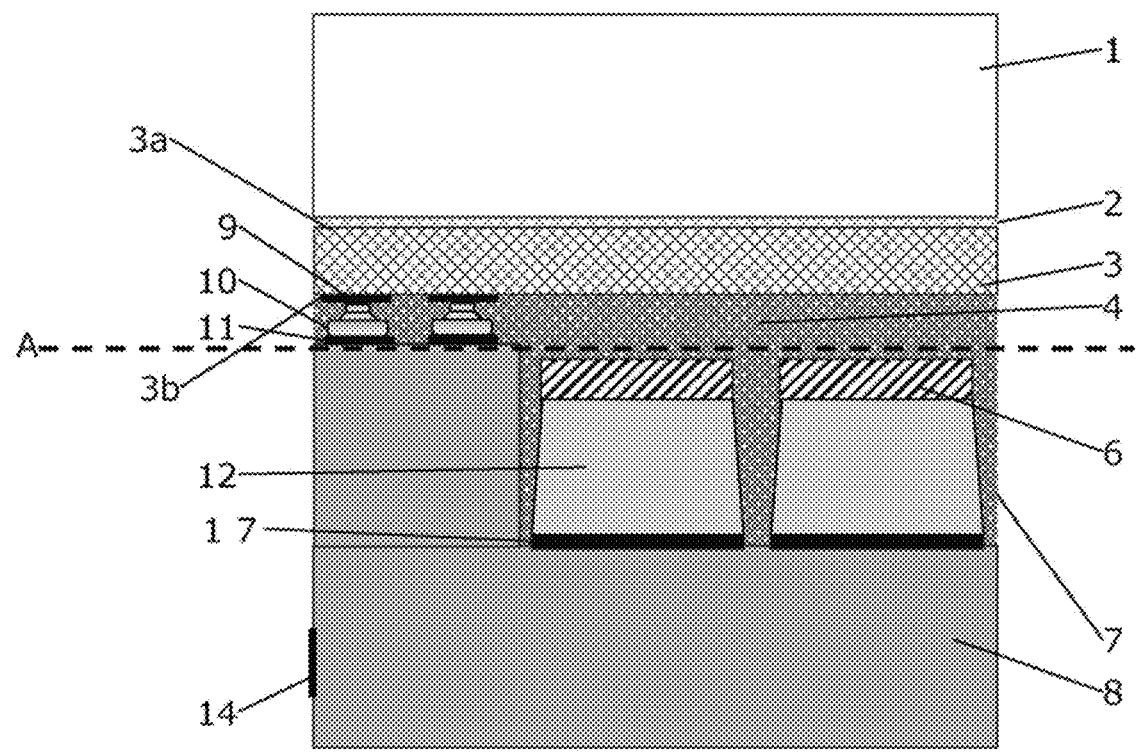

[FIG. 21]
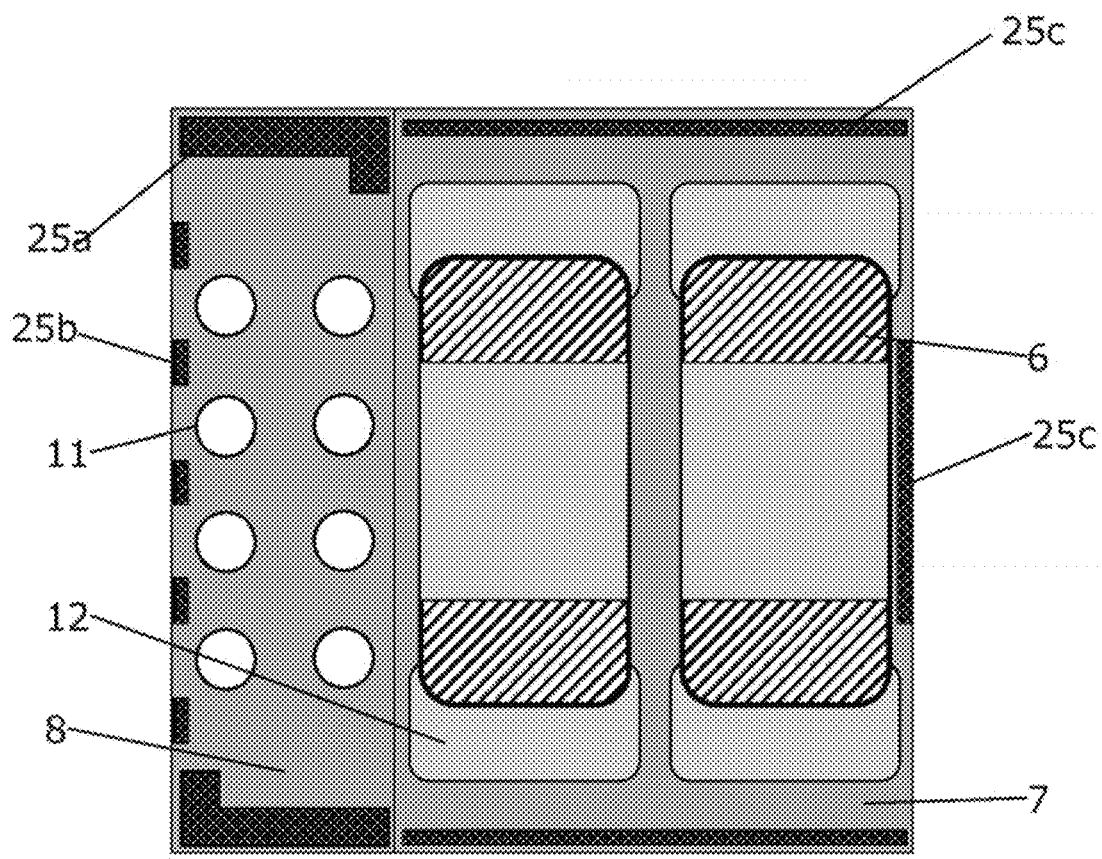

[FIG. 22]
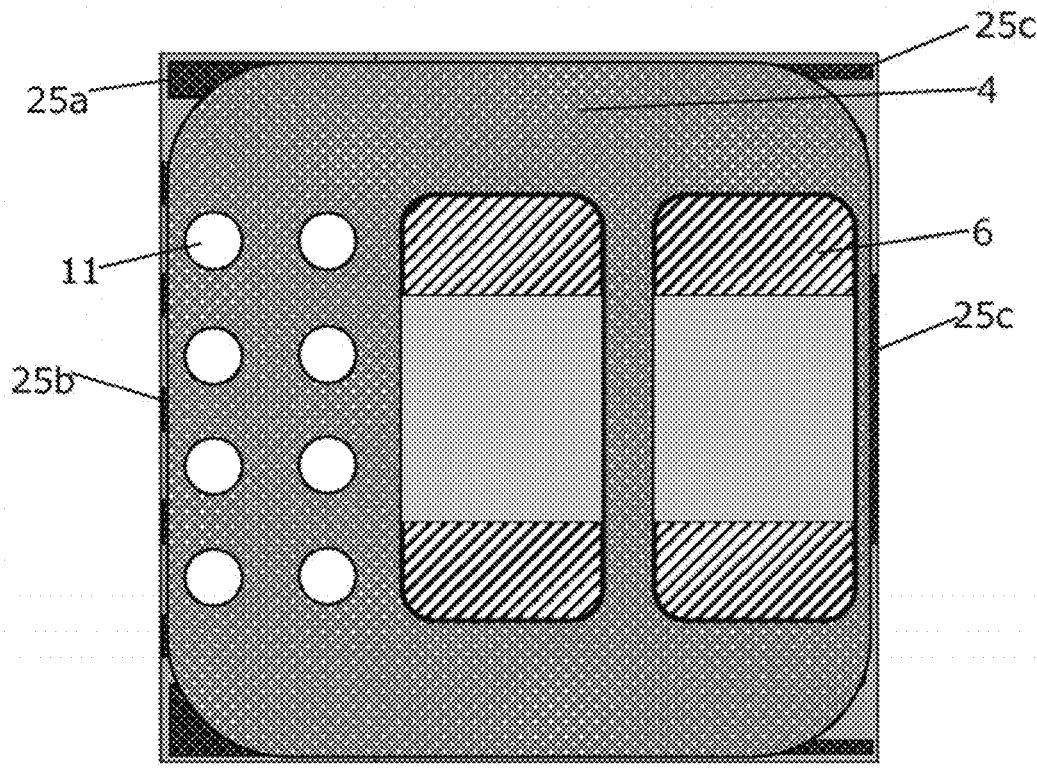
[FIG. 23]
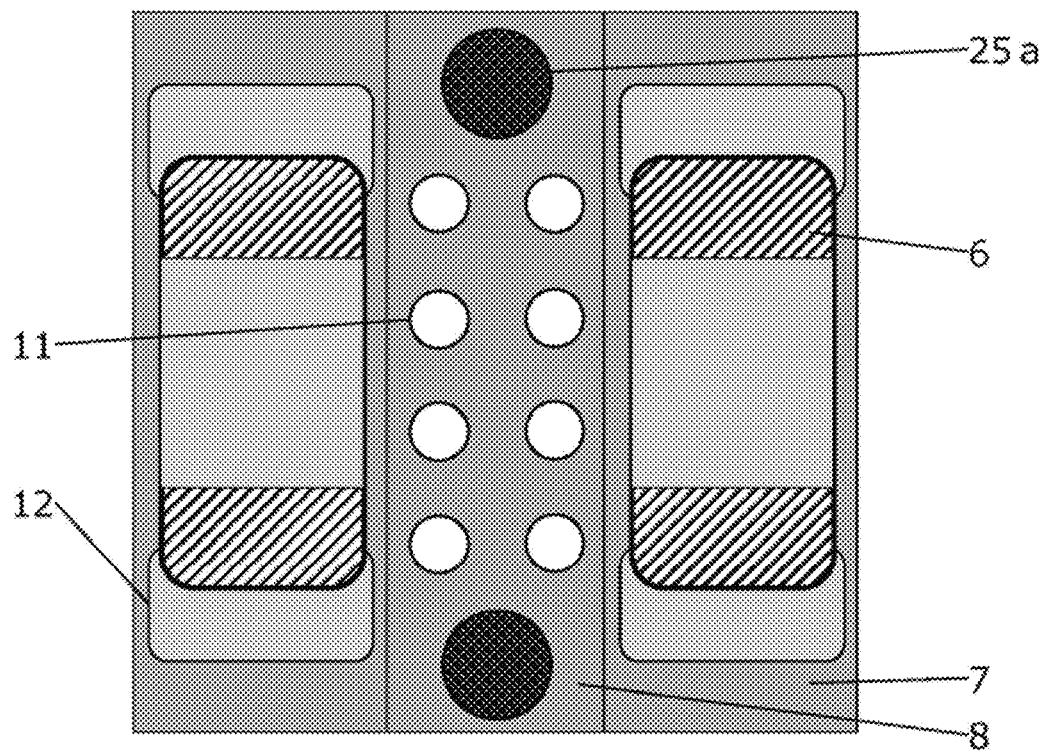

[FIG. 24]
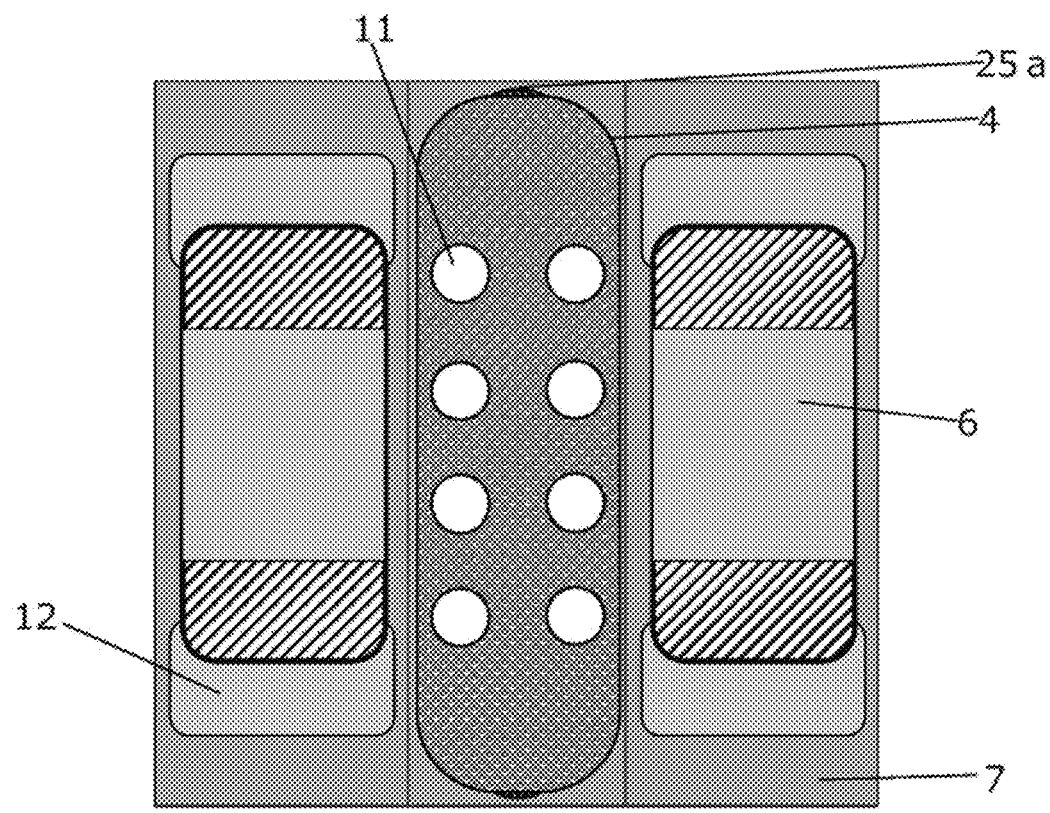
[FIG. 25]
RELATED ART
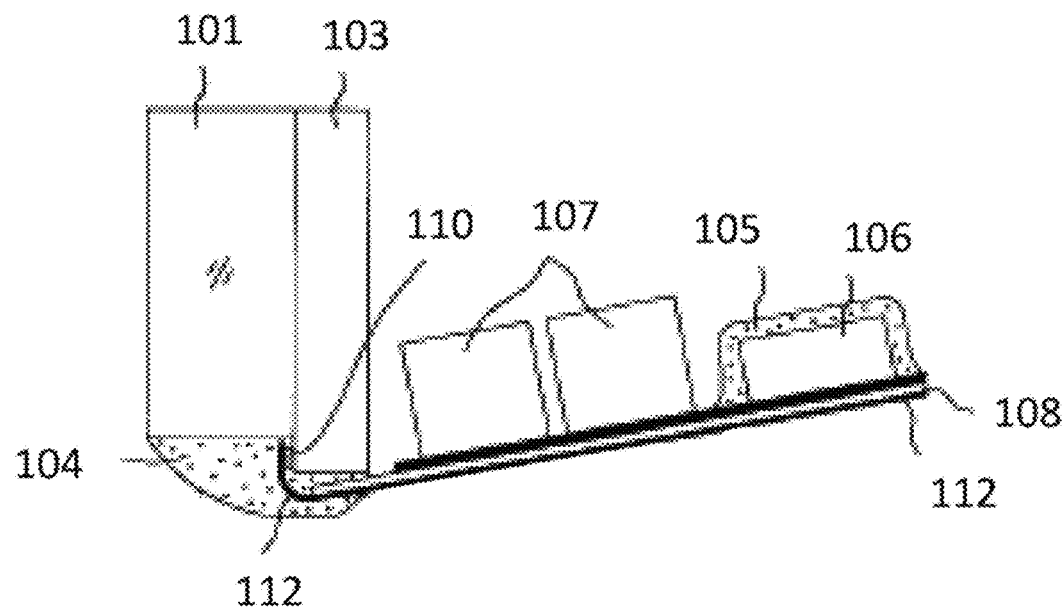

[FIG. 26]
RELATED ART
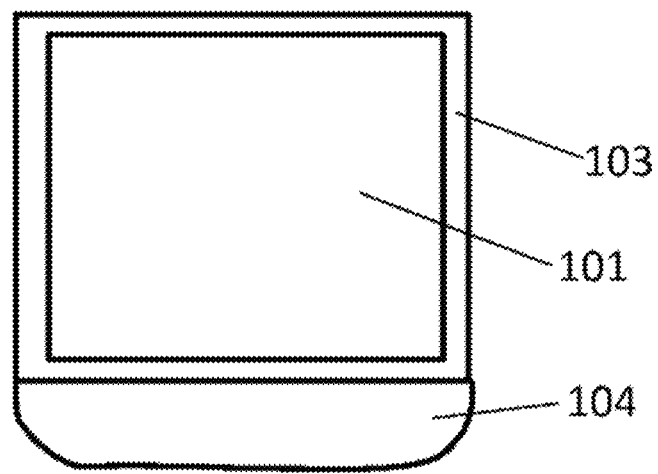

SOLID-STATE IMAGING DEVICE HAVING ELECTRONIC COMPONENTS MOUNTED BETWEEN A MAIN SUBSTRATE AND AN IMAGING ELEMENT

TECHNICAL FIELD

The present disclosure relates to a small-sized solid-state imaging device provided in an electronic endoscope or the like.

BACKGROUND ART

A medical endoscope capable of observing internal organs in a body cavity by inserting a long and thin insertion part into the body cavity and capable of performing various curative treatments by using a treatment tool inserted into a treatment tool channel has been provided in the past in a medical field. Moreover, an industrial endoscope capable of observing or inspecting scratches or corrosion inside a boiler, a turbine, an engine, a chemical plant and so on has been also provided in an industrial field.

In such endoscopes (electronic endoscopes), there is one including a solid-state imaging device having a solid-state imaging element such as a charged-coupled device (abbreviated as CCD) or an electronic component at a tip end of the insertion part. The solid-state imaging device photoelectrically converts reflected light from an imaging object and transmits a photoelectrically-converted signal to an information processor having a monitor device through a signal cable. The information processor processes the signal received from the solid-state imaging device and displays the imaging object imaged by the solid-state imaging device on the monitor device in colors.

The insertion part of the endoscope including the solid-state imaging device is desired to be thin in diameter, for example, for being inserted into a narrow and winding lumen. The solid-state imaging device is desired to be small in size and small in diameter for realizing the endoscope capable of making a small turn with good operability.

In Patent Literature 1, a solid-state imaging device arranged at a tip end of an endoscope is disclosed. The solid-state imaging device formed to be small in size as a whole by making a sealing and fixing part formed by a sealing resin as small as possible is disclosed in Patent Literature 1.

CITATION LIST

Patent Literature

PTL 1: JP-A-2001-17389

SUMMARY OF INVENTION

FIG. 25 is a cross-sectional view of the solid-state imaging device of Patent Literature 1 and FIG. 26 is a plan view of the solid-state imaging device of Patent Literature 1. In the solid-state imaging device of Patent Literature 1, a transparent member 101 is bonded to a light receiving surface of a solid-state imaging element 103, and a lead 112 of a FPC (flexible printed circuit board) is connected to a bump electrode 110 formed on the light receiving surface. Also in the solid-state imaging device of Patent Literature 1, a peripheral part of the transparent member 101 and a connection part between the solid-state imaging element 103 and the lead 112 are sealed by a sealing resin 104.

Accordingly, a portion of the sealing resin 104 excessively protrudes to the periphery in Patent Literature 1. Accordingly, the reduction in size of the solid-state imaging device has been hindered.

An object of the present application is to provide a solid-state imaging device further reduced in size.

In order to solve the above problem, there is provided a solid-state imaging device including a solid-state imaging element and a substrate fixed to the solid-state imaging element by a sealing resin on a surface on an opposite side of a light receiving surface of the solid-state imaging element, in which an outer edge of the substrate seen from the light receiving surface side of the solid-state imaging element is positioned within an outer edge of the solid-state imaging element and an outer edge of the sealing resin seen from the light receiving surface side of the solid-state imaging element is positioned within the outer edge of the solid-state imaging element.

According to the present disclosure, a solid-state imaging device further reduced in size can be provided.

BRIEF DESCRIPTION OF DRAWINGS

FIG. 1 is a cross-sectional view showing a structure of a solid-state imaging device according to Embodiment 1.

FIG. 2 is a plan view showing the structure of the solid-state imaging device according to Embodiment 1.

FIG. 3 shows cross-sectional views showing processes of forming the solid-state imaging device according to Embodiment 1.

FIG. 4 shows cross-sectional views showing processes of forming a solid-state imaging device according to Embodiment 2.

FIG. 5 is a cross-sectional view showing a structure of a solid-state imaging device according to Embodiment 3.

FIG. 6 is a cross-sectional view showing a structure of a solid-state imaging device according to Embodiment 4.

FIG. 7 is a cross-sectional view schematically showing a structure of a solid-state imaging device according to Embodiment 5.

FIG. 8 is a side view schematically showing the structure of the solid-state imaging device according to Embodiment 5.

FIG. 9 is a plan view schematically showing the structure of the solid-state imaging device according to Embodiment 5.

FIG. 10 shows cross-sectional views schematically showing manufacturing processes of the solid-state imaging device according to Embodiment 5.

FIG. 11 is a cross-sectional view schematically showing a shape of a main substrate according to Embodiment 5.

FIG. 12 is a cross-sectional view schematically showing the structure of the solid-state imaging device according to Embodiment 5.

FIG. 13 is a cross-sectional view schematically showing the shape of the main substrate according to Embodiment 5.

FIG. 14 is a cross-sectional view showing a structure of a solid-state imaging device according to Embodiment 6.

FIG. 15 is a cross-sectional view showing the structure of the solid-state imaging device according to Embodiment 6.

FIG. 16 is a plan view showing the structure of the solid-state imaging device according to Embodiment 6.

FIG. 17 is a plan view showing the structure of the solid-state imaging device according to Embodiment 6.

FIG. 18 is a cross-sectional view showing wetting and spreading of a sealing resin according to Embodiment 6.

FIG. 19 shows cross-sectional views showing processes of forming the solid-state imaging device according to Embodiment 6.

FIG. 20 is a cross-sectional view showing a structure of a solid-state imaging device according to Embodiment 7.

FIG. 21 is a plan view showing the structure of the solid-state imaging device according to Embodiment 7.

FIG. 22 is a plan view showing the structure of the solid-state imaging device according to Embodiment 7.

FIG. 23 is a plan view showing a structure of a solid-state imaging device according to Embodiment 8.

FIG. 24 is a plan view showing the structure of the solid-state imaging device according to Embodiment 8.

FIG. 25 is a cross-sectional view showing a structure of a solid-state imaging device in related art.

FIG. 26 is a plan view showing the structure of the solid-state imaging device in related art.

DESCRIPTION OF EMBODIMENTS

Embodiment 1

Hereinafter, Embodiment 1 of the present invention will be explained with reference to the drawings.

FIG. 1 is a cross-sectional view of a solid-state imaging device according to Embodiment 1 of the present disclosure, and FIG. 2 is a plan view of the solid-state imaging device according to Embodiment 1 of the present disclosure.

<Structure>

As shown in FIG. 1, the solid-state imaging device according to Embodiment 1 of the present invention has a solid-state imaging element 3 having a rectangular parallelepiped shape. The solid-state imaging element 3 has a light receiving surface 3a and a back surface 3c.

A transparent member 1 (for example, a cover glass) having a rectangular parallelepiped shape is arranged on the light receiving surface 3a of the solid-state imaging element 3. The transparent member 1 is fixed to the solid-state imaging element 3 by an adhesive 2. A plurality of first connection terminals 9 are formed on the back surface 3c of the solid-state imaging element 3.

The wiring on the light receiving surface 3a is electrically connected to the first connection terminals 9 on the back surface 3c. The same applies to the transparent member 1 according to Embodiment 5.

A convex-shaped main substrate 8 is arranged on the back surface 3c. The solid-state imaging element 3 is fixed to the main substrate 8 by a first sealing resin 4 and a second sealing resin 5.

A plurality of second connection terminals 11 are formed on an upper surface of a protruding part of the main substrate 8. Bump electrodes 10 are formed between the second connection terminals 11 of the main substrate 8 and the first connection terminals 9 formed on the back surface 3c. The bump electrodes 10 electrically connect the main substrate 8 and the solid-state imaging element 3.

A plurality of third connection terminals 17 are formed on an upper surface of a base part of the main substrate 8. A plurality of electronic components 6 having connection terminals 32 are arranged in cavities 7 between the back surface 3c and the base part of the main substrate 8.

Bump electrodes 13 are provided between the third connection terminals 17 and the connection terminals 32. The bump electrodes 13 electrically connect the main substrate 8 and the electronic components 6. The second sealing resin 5 is filled in the cavities 7 to cover the electronic components 6. Connection terminals 15 for cables are formed on a side surface of the base part of the main substrate 8.

Areas of the transparent member 1 and the adhesive 2 in plan view are smaller than an area of the solid-state imaging element 3 in plan view (see FIG. 2). Outer edges of the transparent member 1 and the adhesive 2 are arranged so as to be positioned within an outer edge of the solid-state imaging element 3 in plan view.

Moreover, areas of the first sealing resin 4, the second sealing resin 5 and the main substrate 8 in plan view are smaller than the area of the solid-state imaging element 3 in plan view. Outer edges of the first sealing resin 4 and the second sealing resin 5 and an outer edge of the main substrate 8 are arranged so as to be positioned within the outer edge of the solid-state imaging element 3 in a plan view.

Accordingly, an element having the largest width dimensions in the solid-state imaging device, namely, the largest dimensions in vertical and horizontal directions in FIG. 2 is the solid-state imaging element 3. The solid-state imaging device can be reduced in size to be the same size as the solid-state imaging element 3.

The areas of the transparent member 1 and the adhesive 2 in plan view may be the same as the area of the solid-state imaging element 3 in plan view. Then, shapes of the transparent member 1 and the adhesive 2 in plan view may be the same as a shape of the solid-state imaging element 3 in plan view.

Moreover, the areas of the first sealing resin 4, the second sealing resin 5 and the main substrate 8 in plan view may be the same as the area of the solid-state imaging element 3 in plan view. Then, shapes of the first sealing resin 4, the second sealing resin 5 and the main substrate 8 in plan view may be the same as the shape of the solid-state imaging element 3 in plan view.

<Manufacturing Method>

The solid-state imaging device can be manufactured by processes shown in FIG. 3.

First, the first connection terminals 9 are formed on the back surface 3c as shown in (a) of FIG. 3.

The transparent member 1 is arranged on the light receiving surface 3a of the solid-state imaging element 3 and fixed by the adhesive 2.

On the other hand, the second connection terminals 11 and the third connection electrodes 17 are formed on the main substrate 8, and the bump electrodes 10 are formed on the second connection terminals 11 as shown in (b) of FIG. 3. The connection terminals 32 are formed on the electronic components 6, and the bump electrodes 13 are formed on the connection terminals 32. Moreover, the electronic components 6 are arranged in the cavity 7, and the bump electrodes 13 are connected to the third connection terminals 17 on the main substrate 8. Accordingly, the electronic components 6 are electrically connected to the main substrate 8.

Next, the electronic components 6 are filled with the second sealing resin 5 as shown in (c) of FIG. 3. Next, the main substrate 8 is cut into individual pieces by dicing as shown in (d) of FIG. 3. Sequentially, the first sealing resin 4 is coated on the surface of the main substrate 8 where the bump electrodes 10 are formed as shown in (e) of FIG. 3.

Next, the surface of the main substrate 8 where the bump electrodes 10 are formed is arranged so as to face the surface of the solid-state imaging element 3 where the first connection terminal 9 is formed as shown in (f) of FIG. 3. Then, the bump electrodes 10 are connected to the first connection terminals 9, and the main substrate 8 and the solid-state imaging element 3 are fixed by the first sealing resin 4.

Accordingly, the solid-state imaging element 3 is electrically connected to the main substrate 8. According to the above processes, the solid-state imaging device is completed.

<Operation>

The solid-state imaging element 3 receives light reflected on an imaging object by the light receiving surface 3a through the transparent member 1 and converts the received light into an electric signal.

The electric signal is transmitted to the main electrode 8 that is electrically connected to the solid-state imaging element 3. The electric signal is transmitted to the electronic components 6 electrically connected to the main substrate 8. The electronic components 6 perform given signal processing with respect to the transmitted electric signal and transmit the signal to the main substrate 8. The electric signal transmitted to the main substrate 8 through the electronic components 6 is transmitted to an external apparatus (for example, an information processor including a monitor device) from the connection terminals 15 for cables.

<Respective Elements>

Examples of sizes of respective members are as follows.
Main substrate 8: 1 mm×1 mm×thickness 0.6 mm
Electronic Component 6: 0.6 mm×0.3 mm×thickness 0.3 mm or less
Transparent Member: 1 mm×1 mm×thickness 0.3 mm
Solid-State Imaging Element 3: 1 mm×1 mm×thickness 0.1 mm The area of the transparent member 1 in plan view and the area of the main substrate 8 in plan view may be smaller than the area of the solid-state imaging element 3 in plan view as shown in FIG. 1 and FIG. 2.

<Electronic Component 6>

The electronic component 6 is, for example, a capacitor or a resistor. The electronic component 6 has the connection terminals 32 for giving and receiving the electric signal. The electric components 6 are arranged so as to be positioned within the outer edge of the solid-state imaging element 3 in plan view.

<Transparent Member 1>

The transparent member 1 is a transparent optical member having a rectangular parallelepiped shape. Width dimensions of the transparent member 1 are made to be equal to or smaller than width dimensions of the solid-state imaging element 3 for making the width dimensions of the solid-state imaging device (vertical and horizontal dimensions in plan view of the solid-state imaging device) the same dimensions as the solid-state imaging element 3 to reduce the size.

<Solid-State Imaging Element 3>

The solid-state imaging element 3 is a CCD image sensor or a CMOS image sensor detecting light that converts the light into an electric signal. A circuit that performs signal processing may be incorporated in the solid-state imaging element 3. The solid-state imaging element 3 may also be overlaid on a device having a function of performing signal processing. The solid-state imaging element 3 has the first connection terminals 9 for giving and receiving the electric signal.

<First Connection Terminal 9, Second Connection Terminal 11, Connection Terminals 32, 14>

The first connection terminals 9, the second connection terminals 11 and the connection terminals 32, 17 are formed of, for example, aluminum or the like. It is also preferable to use a metal such as copper having a higher conductivity than aluminum for the first connection terminals 9, the second connection terminals 11 and the connection terminals 32, 17. In the case where the copper is used for the first connection terminals 9, the second connection terminals 11 and the connection terminals 32, 17, nickel-gold plating may be performed to copper to make the copper hardly oxidized.

<Connection Terminals 15 for Cables>

The connection terminals 15 for cables are formed of, for example, aluminum or the like. It is also preferable to use a metal such as copper having a higher conductivity than aluminum for the connection terminals 15 for cables. In the case where the copper is used for the connection terminals 15 for cables, nickel-gold plating may be performed to copper to make the copper hardly oxidized.

<Bump Electrodes 10, 13>

The bump electrodes 10, 13 are formed of, for example, solder. Metals such as copper and gold may be used for the bump electrodes 10, 13.

<Main Substrate 8>

The main substrate 8 is formed of, for example, a ceramic substrate. A build-up substrate, an aramid-epoxy substrate, a glass epoxy substrate or the like may be used for the main substrate 8. In the main substrate 8, the cavities 7 (electronic components 6) for the electronic components 6 being mounted on the left and right are formed in plan view.

<Electronic Component 6>

A size of the electronic component 6 is, for example, 0.6 mm×0.3 mm×thickness 0.3 mm. As the electronic component 6 is positioned within the cavity 7, the width dimensions of the solid-state imaging device can be kept the same as the width dimensions of the solid-state imaging element 3.

Two electronic components 6 are formed adjacent to the protruding part of the main substrate 8 symmetrically. Accordingly, heat dissipation of the solid-state imaging element 3 becomes symmetrical, and in-plane variation in electrical characteristics or the like can be suppressed.

It is also preferable that the electronic components 6 are formed also in a base part 8b (see FIG. 1) of the main substrate 8 to be four-points symmetrical.

<Adhesive 2>

The adhesive 2 is a transparent adhesive such as a UV curable adhesive. Width dimensions of the adhesive 2 are equal to or less than the width dimensions of the transparent member 1.

<First Sealing Resin 4>

The first sealing resin 4 is an epoxy-type adhesive. Width dimensions of the first sealing resin 4 are equal to or less than the width dimensions of the solid-state imaging element 3. The first sealing resin 4 covers the bump electrodes 10 connecting the solid-state imaging element 3 to the main substrate 8.

<Second Sealing Resin 5>

Width dimensions of the second sealing resin 5 are equal to or less than the width dimensions of the solid-state imaging element 3. The second sealing resin 5 has a lower elastic modulus and a higher heat dissipation as compared with the first sealing resin 4. In a surface of the second sealing resin 5 contacting the first sealing resin 4, a taper is formed from an outer side to an inner side as a tapered part 5a as shown in FIG. 1. For example, a boundary surface between the first sealing resin 4 and the second sealing resin 5 inclines in a direction toward which a thickness of the first sealing resin 4 is reduced from the inside to the outside of the solid-state imaging device. The tapered part 5a is provided in this manner, thereby preventing the first sealing resin 4 from leaking at the time of manufacturing.

<Advantages>

When the transparent member 1, the solid-state imaging element 3, the main substrate 8 and the electronic components 6 forming the solid-state imaging device are laminated to be connected as in the above structure, the width dimensions of the solid-state imaging device can be the same as the width dimensions of the solid-state imaging element and the size can be reduced. As the width dimensions of the solid-state imaging device can be made small, for example, an insertion part of an endoscope can be reduced in diameter.

Moreover, two types of resins which are the first sealing resin 4 with high adhesiveness and the second sealing resin 5 with a high heat dissipation are used for the sealing resins for fixing the solid-state imaging device as well as the symmetrical structure is applied, thereby providing the solid-state imaging device with high reliability.

(Second Embodiment): Separation of First Sealing Resin 4 and Second Sealing Resin 5

Next, a second embodiment will be explained with reference to (a) of FIG. 4 to (d) of FIG. 4. The second embodiment differs from Embodiment 1 in the shape of the second sealing resin 5 after sealing. Items not explained are the same as those of Embodiment 1.

<Processes>

First, as shown in (a) of FIG. 4, after the adhesive 2 is applied to the light receiving surface 3a side of the solid-state imaging element 3, the transparent member 1 is arranged and the adhesive is allowed to wet and spread over the entire surface of the light receiving surface 3a, then, fixed by ultraviolet light or heat.

On the other hand, as shown in (b) of FIG. 4, the main substrate 8 is provided with the second connection terminals 11 and the third connection terminals 17, and the bump electrodes 10 are formed on the second connection terminals 11 by heating, pressurizing, ultrasonic waves or the like. The electronic components 6 have the connection terminals 32, and the bump electrodes 13 are formed on the connection terminals 32.

The electronic components 6 are arranged in the cavity 7, and the bump electrodes 13 are connected to the third connection terminals 17 on the main substrate 8 by heat treatment such as reflow. Accordingly, the electronic components 6 are electrically connected to the main substrate 8.

Next, as shown in (c) of FIG. 4, the electronic components 6 on the main substrate 8 on which the electronic components 6 are mounted are filled with the second sealing resin 5. After that, as shown in (d) of FIG. 4, the main substrate 8 is cut by dicing using a cutting blade or the like into individual pieces.

In the process of resin sealing shown in (c) of FIG. 4 and (d) of FIG. 4, the sealing resin is filled around the electronic components 6 mounted on the main substrate 8 by potting or the like.

When the second sealing resin 5 is filled so as not to protrude to side surface parts of adjacent electronic components 6 in the above process, the main substrate 8 can be cut into individual pieces by cutting only the main substrate 8 without cutting the second sealing resin 5 at the time of dicing into individual pieces, and a substrate size and cut parts after cutting can be improved and stabilized in quality.

The second sealing resin 5 is filled to a position not overlapping with upper surfaces of the electronic components 6, thereby stopping wetting and spreading of the first sealing resin 4 at end parts of the electronic components 6 at the time of mounting the solid-state imaging element 3 as shown in (f) of FIG. 4 after the first sealing resin 4 is applied as shown in (e) of FIG. 4.

<Structure>

In the structure of Embodiment 2, the first sealing resin 4 and the second sealing resin 5 are separated from each other. That prevents the first sealing resin 4 from flowing out to outer sides of the electronic components 6 and an outer side of the main substrate 8, which realizes a small-sized structure of the solid-state imaging device.

(Embodiment 3) First Sealing Resin 4 has Barrel Shape

Next, Embodiment 3 will be explained with reference to FIG. 5. Embodiment 3 differs from Embodiment 2 in a shape of the first sealing resin 4. Items not explained are the same as those of Embodiments 1, 2.

The shape of the first sealing resin 4 differs depending on wettability between the first sealing resin 4 and the solid-state imaging element 3. The shape of the first sealing resin 4 is not limited to a fillet shape shown in (f) of FIG. 4 in Embodiment 2 but may be a barrel shape as shown in FIG. 5.

The wettability of the first sealing resin 4 with respect to surfaces of the main substrate 8 and the solid-state imaging element 3 is reduced. Moreover, viscosity of the first sealing resin 4 is increased. According to the above, a central part of the first sealing resin 4 is extruded to form the barrel shape at the time of mounting the solid-state imaging device 3 onto the main substrate 8. Accordingly, stress applied in heat treatment or a reliability test in a post-process can be absorbed more.

(Embodiment 4) Third Sealing Resin 26

Next, Embodiment 4 will be explained with reference to FIG. 6. In Embodiment 4, the function of preventing flow-out of the first sealing resin 4 in Embodiments 2 and 3 is improved and a second connection between the electronic components 6 and the solid-state imaging element 3 is added. Items not explained are the same as Embodiments 1 to 3.

As a method of further improving the function of preventing flow-out of the first sealing resin 4 and improving reliability in the connection between the main substrate 8 and the solid-state imaging element 3, a structure in which a third sealing resin 26 different from the first sealing resin 4 is formed over the electronic components 6 is applied.

The third sealing resin 26 is a material different from the first sealing resin 4, which is a resin with a lower elastic modulus and a higher heat dissipation as compared with the first sealing resin 4.

The third sealing resin 26 is applied onto the electronic components 6 by potting or the like after the main substrate 8 is cut into individual pieces, which is heated at approximately 100° C. to 150° C. to be temporarily cured. After that, when the first sealing resin 4 is applied and the solid-state imaging element 3 is mounted, the first sealing resin 4 wets and spreads, then, a wetting and spreading portion contacts the third sealing resin 26 and stops there, thereby preventing the resin from flowing over to the outer side of the main substrate 8.

After that, the first sealing resin 4 and the third sealing resin 26 are cured by heating at approximately 170° C. to 200° C.

Accordingly, it is possible to positively stop the flow-out of the first sealing resin 4 by the third sealing resin 26.

Furthermore, the solid-state imaging element 3 is connected merely by the metal bumps formed on the central protruding part of the main substrate 8 and the first sealing resin 4 in Embodiments 2, 3; however, spaces above the electronic components are filled with the third sealing resin 26 for securing connection with higher quality to connect the main substrate 8 to the solid-state imaging element 3 in Embodiment 4.

As for the third sealing resin 26, not only a thermosetting resin but also a UV curable resin capable of being cured in a short time or a resin combining a thermosetting type and a UV-curable type may be used.

Embodiment 5

(Structure of Solid-State Imaging Device)

FIG. 7 is a cross-sectional view schematically showing a structure of a solid-state imaging device according to Embodiment 5.

<Solid-State Imaging Element 3>

As shown in FIG. 7, the solid-state imaging device according to Embodiment 5 includes a rectangular solid-state imaging element 3. FIG. 8 is a side view schematically showing the structure of the solid-state imaging device according to Embodiment 5.

The light receiving surface 3a is provided on one surface of the solid-state imaging element 3 and a rewiring layer is provided on the other back surface 3c.

Wirings on both surfaces of the solid-state imaging element 3 are electrically connected to each other by through vias 3b. When the light receiving surface 3a and the back surface 3c are connected by the through vias 3b, the wiring on the back surface 3c side is rewired so as to correspond to the through vias 3b. The wiring on the light receiving surface 3a side is allowed to correspond to the wiring on the back surface 3c. The same applies to other embodiments.

Here, the solid-state imaging element 3 is an element that detects light and converts the light into an electric signal or an image, which is, for example, a CCD image sensor, a CMOS image sensor or the like. The solid-state imaging element 3 is formed of a base material such as Si, InGaAs, Inp and InAs.

The number of pixels in the light receiving surface 3a is, for example, one to four million pixels, and a pixel size is, for example, 1 to 2 μm.

The through vias 3b are formed of a metal film or metal plating, and, for example, Cu, W, Au or the like is used.

Here, the inside of the back surface 3c is three-dimensionally wired, and the through vias 3b are electrically connected to the plural first connection terminals 9 on a surface of the back surface 3c. Accordingly, after electric signals of one pixel to plural pixels received by the light receiving surface 3a are processed, the signals can pass through the back surface 3c through the through vias 3b to be transmitted to the first connection terminals 9. Here, the back surface 3c is formed of a wiring layer formed of a metal film made of, for example, Cu, Al, Au or the like, and an insulating layer formed of, for example, epoxy, polyimide, acrylic, SiN, SiO2 or the like.

The first connection terminals 9 are formed of a metal film made of, for example, Au, Al, Cu or the like having a circular shape or a polygonal shape.

On the light receiving surface 3a of the solid-state imaging element 3, the transparent and rectangular parallelepiped-shaped transparent member 1 is arranged, and the transparent member 1 is fixed to the solid-state imaging element 3 by the adhesive 2. Here, a transparent material with a refractive index of 1.3 to 1.8 such as borosilicate, quartz, sapphire or crystal is used for the transparent member 1.

The adhesive 2 is a thermosetting transparent material or a material combining thermosetting and UV-curable materials with a transmittance of 90% or more and a refractive index of 1.3 to 1.8 such as acrylic, epoxy or silicone. The transparent member 1 bonded to the solid-state imaging element 3 prevents dust or foreign matter from directly adhering to the light receiving surface in assembly processes as well as preventing moisture from entering and preventing foreign matter from adhering under use environment.

<Main Substrate 8>

Furthermore, the main substrate 8 is arranged so as to face the back surface 3c of the solid-state imaging element 3. The main substrate 8 is a multistage substrate, for example, formed by two stages. The main substrate 8 is formed by the protruding part 8a with a rectangular parallelepiped shape and the base part 8b with a rectangular parallelepiped shape larger than the protruding part 8a. Both parts form a laminated body or an integral body. On the upper surface of the protruding part 8a and on the upper surface, the side surface and a back surface of the base part 8b, the second connection terminals 11, the third connection terminals 17, the connection terminals 15 and connection terminals 16 are respectively provided, and respective terminals are electrically connected by the three-dimensional wiring and vias inside or on the surface of the main substrate 8.

Here, the main substrate 8 is a relay substrate for connecting terminals for electric signals outputted from the solid-state imaging element 3 and cables for connecting to not-shown external connection devices to a capacitor, a coil and a resistor.

The main substrate 8 is a ceramic multilayer substrate formed of, for example, alumina, glass or the like, or an organic multilayer substrate formed of, for example, glass epoxy, aramid or the like. The connection terminals on the main substrate 8 are formed of a fired conductive adhesive, a plating film with respect to a sputtered film or the like.

The plural second connection terminals 11 are provided on the upper surface of the protruding part 8a of the main substrate 8 at positions facing the first connection terminals 9 of the solid-state imaging element 3. The second connection terminals 11 and the first connection terminals 9 are electrically connected by the bump electrodes 10. Here, the bump electrodes 10 are formed of, for example, Au, Cu, solder, AuSn, a conductive adhesive, nano paste, plating or the like.

Moreover, the first sealing resin 4 is provided between the solid-state imaging element 3 and the main substrate 8, and performs sealing so as to cover the bump electrodes 10. The first sealing resin 4 is a thermosetting or UV curable one-part adhesive formed of a base resin, a hardener, an inorganic filler and the like, and, for example, epoxy, acrylic and silicone resin are used.

On the other hand, the plural third connection terminals 17 are formed on the upper surface of the base part 8b of the main substrate 8, the electronic components 6 are mounted on the third connection terminals 17, and the third connection terminals 17 and the electronic components 6 are electrically connected by a joining material 23.

The electronic components 6 are, for example, the capacitor, the resistor and the coil. For example, components having sizes of 0603, 0402, 0201 and so on are used. The joining material 23 is formed of, for example, solder, AuSn, the conductive adhesive or the like.

A plurality of connection terminals 15 for cables are formed on the side surface of the base part 8b of the main substrate 8. The connection terminals 15 for cables are formed of, for example, Au—Ni, Au—Pd—Ni, Cu or the like, which can be electrically connected to wirings of not-shown connection cables through the solder or the conductive adhesive.

FIG. 9 is a plan view schematically showing a structure of the solid-state imaging element 3 according to the embodiment of the present disclosure.

The light receiving surface 3a formed on the solid-state imaging element 3 is provided in a square shape, and the plural through vias 3b are arranged in an outer peripheral part so as to surround the light receiving surface 3a. The through vias 3b are provided with a pitch distance of, for example, 10 to 100 μm. As the adhesive 2 and the transparent member 1 provided so as to cover the light receiving surface 3a of the solid-state imaging element 3 are formed of a transparent material, light is transmitted and the light receiving surface 3a and electrode pads on the through vias 3b can be observed.

<Advantages>

According to the structure in the embodiment of the present invention, lamination can be performed three-dimensionally while keeping external dimensions within a projected area of the solid-state imaging element in the small and high-image quality solid-state imaging element; therefore, the solid-state imaging device can be formed small in size, and an external form of the tip end of the endoscope can be small.

<Method of Manufacturing Solid-State Imaging Device>

(a1) to (d2) of FIG. 10 are cross-sectional views schematically showing manufacturing processes of the solid-state imaging device according to Embodiment 5 of the present invention.

First, in a process of forming bumps shown in (a1) of FIG. 10, the bump electrodes 10 are formed in the second connection terminals 11 on the protruding part 8a of the main substrate 8 by using a means for forming bumps such as a stud bump bonder.

In a process of mounting the electronic components shown in (b1) of FIG. 10, the joining material 23 as a solder paste is applied to the third connection terminals 17 by using a means for supplying the material such as a dispenser and a needle transfer device, then, the electronic components 6 are mounted and joined by solder by using a means for melting solder such as a reflow furnace.

A description has been made in which the process of the electronic components is performed after the process of forming bumps; however, the order is not limited to this. It is also possible to perform the process of forming bumps after the process of the electronic components.

Furthermore, in a process of applying the sealing resins shown in (c1) of FIG. 10, the first sealing resin 4 is applied to the protruding part 8a of the main substrate 8 by using the means for supplying the material such as the dispenser and the needle transfer device. Here, the second sealing resin 5 may be applied in advance so as to fill in clearances between the protruding part 8a of the main substrate 8 and the electronic components 6. As a bonding area is increased by the second sealing resin 5, the reliability can be improved.

Next, in a process of mounting the solid-state imaging element shown in (d1) of FIG. 10, the first sealing resin 4 is cured while joining the bump electrodes 10 and the first connection terminals 9 by using a heating/pressurizing means. For example, a temperature at joining parts is preferably 120 to 180° C. It is also preferable to apply ultrasonic waves at the same time as heating/pressurization. It is possible to perform joining at a low temperature and the process can be applied to the solid-state imaging element 3 with low heat-resistance properties. It is further preferable to perform heating by using a heating means such as a curing furnace or the reflow furnace. It is possible to cure plural solid-state imaging devices at once to thereby shorten a production lead time.

(a2) to (d2) of FIG. 10 are side views of the above (a1) to (d1) of FIG. 10, respectively.

<Shape, Cutout, Chamfering of Main Substrate 8>

FIG. 11 is a cross-sectional view schematically showing the shape of the main substrate 8 according to Embodiment 5. A first cutout part 8c is provided in at least one place in the vicinity of the top of the protruding part 8a of the main substrate 8. It is preferable to further provide a second cutout part 8d in at least one place in the vicinity of the top of the base part of the main substrate 8.

FIG. 12 is a cross-sectional view schematically showing the structure of the solid-state imaging device according to Embodiment 5. The first sealing resin 4 existing between the solid-state imaging element 3 and the protruding part 8a of the main substrate 8 wets and spreads along the first cutout part 8c before wetting and spreading to an outer peripheral part of the back surface 3c. Accordingly, the first cutout part 8c is filled with the first sealing resin 4. As a result, the first sealing resin 4 does not wet and spread to a side surface of the solid-state imaging element 3.

On the other hand, the second sealing resin 5 existing between the base part 8b and the protruding part 8a of the main substrate 8 wets and spreads inside the second cutout part 8d. However, the sealing resin 5 does not wet a side surface of the main substrate 8.

Here, in a case where application amounts of the first sealing resin 4 and the second sealing resin 5 are small and there are many clearances between the solid-state imaging element 3 and the main substrate 8, bonding strength between the solid-state imaging element 3 and the main substrate 8 is dominated by an effect of joining strength of the bump electrodes 10. Accordingly, there arises a problem that joining strength between the solid-state imaging element 3 and the main substrate 8 is reduced to a degree not withstanding vibration at the time of conveying in assembly processes or an impact received when the solid-state imaging device falls to cause breakdown failures. The problem becomes prominent particularly in a case where the number of terminals of the second connection terminals 11 on the protruding part 8a of the main substrate 8 is small such as several pins or several dozen pins, or in a case where the second connection terminals 11 are arranged at positions biased to the center of the main substrate 8.

For the above reasons, it is required that the sealing resin does not protrude from the external form of the solid-state imaging element 3 and the clearances are sufficiently filled with the sealing resin.

<Shape>

Here, a shape of the first cutout part 8c and the second cutout part 8d in FIG. 11 and FIG. 12 will be explained. The shape of the cutout parts is a concave shape, namely, a half-dome shape. It is preferable that widths in a width direction and a depth direction are equivalent, and that a depth is ½ of the width to equivalent to the width in FIG. 11 and FIG. 12.

An end surface of the cutout part preferably has a smooth dome shape, and further preferably has minute unevenness and certain surface roughness. This has an effect of suppressing wetting and spreading to the side surface as a surface tension of the sealing resin is increased due to the increase in surface area.

Furthermore, the depth is defined by setting a width of the main substrate is w1, a width of a top part is w2, a width of the first cutout part 8c is w4 and a width of the second cutout part 8d is w3. The relationship of them is explained below.

The width w4 of the first cutout part 8c is desirably 5% or more to 50% or less of the width of the top part w2. When the width is lower than 5%, there arises a problem that the first sealing resin 4 wets and spreads over the entire back surface of the back surface 3c to protrude to the side surface. On the other hand, when the width is larger than 50%, the first cutout part 8c can be provided only on one side of the top part, which forms the sealing resin with an unsymmetrical fillet shape.

On the other hand, the wider the width w4 of the first cutout part, the more the effect of introducing the first sealing resin 4 to a direction of the base part 8 is increased, which can suppress flowing of the sealing resin to the side surface of the solid-state imaging element 3. It is further preferable that an angle made by the first cutout part 8c and the top part is 30 degrees or more to 60 degrees or less. The first sealing resin 4 is thereby allowed to flow to the base part 8b side.

On the other hand, the width w3 of the second cutout part is desirably 2% or more to 30% or less of the width w1 of the main substrate 8. When the width is lower than 2%, there arises a problem that the second sealing resin 5 protrudes from the main substrate 8 and projected dimensions from the upper surface of the cover glass exceeds the solid-state imaging element 3 to hinder the size reduction. When the width is larger than 30%, there arise problems that it is difficult to secure a mounting area and further the sealing resin flows out to the end surface of the main substrate 8.

<Advantages>

As the first cutout part 8c and the second cutout part 8d as described above are formed in at least one corner, it is possible to prevent spreading and wetting to the end surface of the sealing resin. As a result, the spreading of the first sealing resins 4, 5 can be suppressed within a range of the projected area of the solid-state imaging element 3, which contributes to the reduction in size.

Furthermore, the first cutout parts 8c and the second cutout parts 8d are provided at four corners, thereby allowing spreading shapes to be uniform and obtaining an effect of alleviating stress distribution after joining. It is also preferable that not only the first cutout parts 8c and the second cutout parts 8d but also plural cutout parts are provided at an intermediate part of an edge, and cutout parts can be provided in all edges.

<Method of Forming Cutout Parts>

Next, a method of forming the first cutout part 8c and the second cutout part 8d will be described.

After the main substrates 8 made of ceramic are fired and cut into individual pieces, the main substrates 8 are put in a chemical resistant net all together and vibration is added for a certain period of time. As the adjacent main substrates 8 collide with one another, stress is concentrated on corner parts and an impact exceeding breakdown strength is added to corner parts.

According to the above, the corner parts fall off and the first cutout parts 8c and the second cutout parts 8d are formed. After that, the entire net is put in a plating bath and electroless plating is performed, thereby forming plating on the connection terminals. It is also preferable to form cutout parts by adding vibration at the time of being put in the plating bath or at the time of washing. It is thus possible to reduce production time.

According to the above Embodiment 5, a ceramic substrate with 0.90 to 0.98 mm×0.90 to 0.98 mm with a height 0.85 to 0.95 mm was formed and the cutout parts were formed, as a result, widths of the first cutout parts 8c and the second cutout parts 8d were formed to have 0.05 mm to 0.20 mm.

Two electronic components 6 of 0603 were mounted, and the first sealing resin 4 and the second sealing resin 5 were applied to the top part of the main substrate 8, then, the solid-state imaging element 3 with 1.0 mm×1.0 mm×0.4 mm was mounted by thermocompression bonding with a mounting accuracy ±5 µm, as a result, the first sealing resin 4 and the second sealing resin 5 could perform sealing without protruding from the main substrate 8 and without forming holes; therefore, the projected area of the solid-state imaging device could be suppressed within 1.0×1.0 mm that is equivalent to dimensions of the solid-state imaging element 3.

Though the net in the above embodiment has been explained as one capable of housing a plurality of main substrates 8, the net is not limited to this. It is also preferable that partitions capable of housing the main substrates 8 one by one are provided inside the net and that protrusions or grinding blades are provided inside the partitions. According to the method, the shape of the cutout parts can be further stabilized.

It is also possible to form the cutout parts by using a machining means such as grinding or a Leutor after fixing individual pieces of the main substrates 8 without using the net. Even when the material of the main substrate 8 is an organic substrate with high breakdown strength such as glass epoxy, the cutout parts can be formed.

<Main Substrate 8 with Inclined Shape>

FIG. 13 is a cross-sectional view schematically showing a shape of the main substrate 8 according to Embodiment 5 of the present invention. The example differs from the above embodiments in a point that side surfaces of the main substrate 8 are inclined.

An angle made by an upper surface and a side surface of the top part of the main substrate 8 is set to θ1, and an angle made by an upper surface and a side surface of the base part 8b of the main substrate 8 is set to θ2.

Here, it is preferable that θ1 and θ2 are lower than 90 degrees. When these angles are lower than 90 degrees, it is possible to suppress flow-out of the first sealing resin 4 in a liquid state to the side surface after wetting and spreading to the outer peripheral part.

On the other hand, when these angles are 90 degrees or more, the first sealing resin 4 wets and spreads to the side surface, which causes problems that the external form is increased in size and solder joining of the connection terminals 15 for cables is hindered.

Furthermore, in a case where cables are connected to the connection terminals 15, there are advantages that the size is easy to be suppressed within the projected amount of the solid-state imaging element 3 even when a fillet amount of solder is increased and that both the size reduction and reliability of the cable connection terminals can be realized by setting θ2 to be lower than 90 degrees.

Embodiment 6

FIG. 14, FIG. 15 are cross-sectional views of a solid-state imaging device according to Embodiment 6 of the present invention.

FIG. 16, FIG. 17 are plan views of the solid-state imaging device at a dashed line A of FIG. 14 according to Embodiment 6 of the present invention. FIG. 16 is a view before sealing and FIG. 17 is a view after sealing.

FIG. 18 is a cross-sectional view showing wetting and spreading of the sealing resin at an area B in FIG. 14 according to Embodiment 6 of the present invention.

<Structure>

In a structure of the solid-state imaging device according to Embodiment 6 of the present invention, there are the solid-state imaging element 3, the light receiving surface 3a is provided on one surface of the solid-state imaging element 3 and the plural first connection terminals 9 are provided on the other surface as shown in FIG. 14, FIG. 15.

The transparent member 1 is arranged so as to face the light receiving surface 3a, and the solid-state imaging element 3 and the transparent member 1 are fixed by the adhesive 2.

The main substrate 8 is arranged so as to face the back surface 3c of the solid-state imaging element 3, the first connection terminals 9 of the solid-state imaging element 3 and the second connection terminals 11 of the main substrate 8 are electrically connected through the bump electrodes 10. A connection part between the solid-state imaging element 3 and the main substrate 8 is fixed by the first sealing resin 4.

Then, the first sealing resin 4 wets and spreads without flowing down to outer sides of first conductor patterns 25a formed at end parts of a joined part as shown in FIG. 17.

Here, the first conductor patterns 25a are also used as recognition marks for positioning in a mounter used when connecting the main substrate 8 and the solid-state imaging element 3. The first conductor patterns 25a have a different shape from that of the second connection terminals 11.

Moreover, the plural electronic components 6 are arranged in the cavities 7 formed on both sides of the joined part between the main substrate 8 and the solid-state imaging element 3 as shown in FIG. 15. The electronic components 6 are electrically connected to the third connection terminals 17 through a joining material 12 on the main substrate 8.

Furthermore, the second connection terminals 14 for plural cables are formed in the main substrate 8.

<Manufacturing Method>

The solid-state imaging device can be manufactured by processes shown in FIG. 19.

First, the first connection terminals 9 are formed in the solid-state imaging element 3 and the transparent member 1 is arranged on the light receiving surface of the solid-state imaging element 3 to be fixed by the adhesive 2 as shown in (a) of FIG. 19.

On the other hand, as shown in (b) of FIG. 19, the first conductor patterns 25a, the second connection terminals 11, the third connection terminals 17 and the second connection terminals 14 for cables are formed on the main substrate 8 in which the cavities 7 are formed.

The first conductor patterns 25a are formed in the same process as the second connection terminals 11, the third connection terminals 17 and the second connection terminals 14 for cables.

Next, the bump electrodes 10 are formed on the second connection terminals 11, and the electronic components 6 and the joining material 12 are arranged on the third connection terminals 17 in the cavities 7 as shown in (c) of FIG. 19.

Next, as shown in (d) of FIG. 19, the joining material 12 is melted by heating to thereby electrically connect the electronic components 6 and the third connection terminals 17 through the joining material 12.

Next, as shown in (e) of FIG. 19, the surface of main substrate 8 in which the bump electrodes 10 are formed is arranged so as to face the surface of the solid-state imaging element 3 on which the first connection terminals 9 are formed, thereby electrically connecting the first connection terminals 9 and the second connection terminals 11 through the bump electrodes 10.

Lastly, the joined part between the first connection terminals 9 and the second connection terminals 11 is sealed with the first sealing resin 4 to thereby fix the connection part as shown in (f) of FIG. 19, then, the solid-state imaging device is completed.

<Operation>

In FIG. 14, the solid-state imaging element 3 receives light at the light receiving surface 3a through the transparent member 1, and the light is converted into an electric signal.

The converted electrical signal is transferred to the main substrate 8 electrically connected to the solid-state imaging element 3.

The electric signal transferred to the main substrate 8 is transferred to the electronic components 6 electrically connected to the main substrate 8.

The electronic components 6 perform processing incorporated in the electronic components 6 with respect to the transferred electric signal, then, transmits the signal to the main substrate 8 again.

The electric signal is transferred to external devices from the second connection terminals 14 for cables after passing through all the electronic components 6.

<Respective Elements>

Concerning sizes of respective members, the main substrate 8 has 1 mm×1 mm×thickness 0.6 mm, the electronic component 6 has 0.6 mm×0.3 mm×thickness 0.3 mm or less, the transparent member 1 has 1 mm×1 mm×thickness 0.3 mm, and the solid-state imaging element 3 has 1 mm×1 mm×thickness 0.1 mm. These sizes are examples.

<Electronic Component 6>

The electronic component 6 is, for example, a capacitor or a resistor.

<Transparent Member 1>

The transparent member 1 is a transparent optical member having a rectangular parallelepiped shape.

Width dimensions of the transparent member 1 are equal to or lower than those of the solid-state imaging element 3 so that width dimensions of the solid-state imaging device are the same as those of the solid-state imaging element 3 to reduce the size.

<Solid-State Imaging Element 3>

The solid-state imaging element 3 is a CCD image sensor or a CMOS image sensor that detects light and converts the light into an electric signal. A circuit performing signal processing may be incorporated. The solid-state imaging element 3 is laminated on an element having a function of performing signal processing. The solid-state imaging element 3 is provided with the first connection terminals 9 for giving and receiving the electric signal.

<First Connection Terminals 9, Second Connection Terminals 11>

The first connection terminals 9 and the second connection terminals 11 are formed of, for example, aluminum or the like; however, a metal such as copper having a higher conductivity than aluminum or tungsten may be used. It is also preferable that nickel/gold plating is applied to copper so as not to be oxidized easily.

<Second Connection Terminals 14 for Cables>

The second connection terminals 14 for cable are formed of, for example, aluminum; however, a metal such as copper having a higher conductivity than aluminum or tungsten may be used. It is also preferable that nickel/gold plating is applied to copper so as not to be oxidized easily.

<Bump Electrodes 10>

The bump electrodes 10 are formed of, for example, solder; however, a metal such as copper or gold may be used.

<Main Substrate 8>

The main substrate 8 is formed of, for example, a ceramic substrate; however, the build-up substrate, the aramid-epoxy substrate, the glass epoxy substrate or the like may be used.

<Cavity 7>

A size of the cavity 7 is 1.0 mm×0.35 mm×thickness 0.35 mm. As the electronic component 6 is positioned within the cavity 7, width dimensions of the solid-state imaging device can be kept the same as width dimensions of the solid-state imaging element 3.

Two cavities 7 are formed symmetrically on the surface of the main substrate 8 connected to the solid-state imaging element 3. As the heat dissipation of the solid-state imaging element 3 is symmetrical, in-plane variation in characteristics can be suppressed.

<Adhesive 2>

The adhesive 2 is a transparent adhesive such as the UV curable adhesive, having width dimension equivalent to or less than those of the solid-state imaging element.

<First Sealing Resin 4>

The first sealing resin 4 is an epoxy-type adhesive, having width dimensions equivalent to or less than those of the solid-state imaging element 3.

The first conductor patterns 25a are formed at end parts of the main substrate 8 as shown in FIG. 16, thereby preventing the first sealing resin 4 from flowing down to outer sides of the first conductor patterns 25a formed at the end parts of the joined part as shown in FIG. 17 and FIG. 18. Moreover, plating processing is applied to the first conductor patterns 25a, thereby allowing the first sealing resin 4 to wet and spread to end parts of the first conductor patterns 25a to form a fillet C.

The first sealing resin 4 may be formed in an area of the cavity 7 as long as the first sealing resin 4 does not flow down to the outer side of the main substrate 8.

<First Conductor Pattern 25a>

The first conductor patterns 25a are formed of, for example, aluminum or the like; however, a metal such as copper having a higher conductivity than aluminum or tungsten may be used. It is also preferable that nickel/gold plating is applied to copper so as not to be oxidized easily.

Moreover, the first conductor patterns 25a are also used as recognition marks for positioning in the mounter used when connecting the main substrate 8 and the solid-state imaging element 3. The first conductor patterns 25a preferably have a different shape from that of the second connection terminals 11 and a shape whereby the first sealing resin 4 does not fall down to the outer side of the main substrate 8, which are corner marks each having a size of 0.3 mm×0.1 mm in a longitudinal direction and 0.15 mm×0.1 mm in a short-side direction.

Embodiment 7

FIG. 20 is a cross-sectional view of a solid-state imaging device according to Embodiment 7 of the present invention, and FIG. 21, FIG. 22 are plan views of the solid-state imaging device at a dashed line A of FIG. 20 according to Embodiment 7 of the present invention, in which FIG. 21 is a view before sealing and FIG. 22 is a view after sealing. Items not explained are the same as those of Embodiment 6.

<Structure>

The structure of the solid-state imaging device according to Embodiment 7 of the present invention includes the solid-state imaging element 3, the light receiving surface 3a provided on one surface of the solid-state imaging element 3 and the plural first connection terminals 9 provided on the other surface as shown in FIG. 20.

The transparent member 1 is arranged so as to face the light receiving surface 3a, and the solid-state imaging element 3 and the transparent member 1 are fixed by the adhesive 2.

The main substrate 8 is arranged so as to face the back surface 3c of the solid-state imaging element 3, and the first connection terminals 9 of the solid-state imaging element 3 and the second connection terminals 11 of the main substrate 8 are electrically connected through the bump electrodes 10. The connection part between the solid-state imaging element 3 and the main substrate 8 is fixed by the first sealing resin 4.

The plural electronic components 6 are arranged in the cavity 7 formed on one side of the joined part between the main substrate 8 and the solid-state imaging element 3, which are electrically connected to the third connection terminals 17 through the joining material 12 on the main substrate 8.

Furthermore, the second connection terminals 14 for plural cables are formed in the main substrate 8.

<Cavity>

A size of the cavity 7 is 1.0 mm×0.7 mm×thickness 0.35 mm. As the electronic components 6 are positioned within the cavity 7, width dimensions of the solid-state imaging device can be kept the same as width dimensions of the solid-state imaging element 3.

One cavity 7 is formed on one side of the second connection terminals 11 between the main substrate 8 and the solid-state imaging element 3. The number of cavities 7 is reduced, thereby shortening manufacturing processes of the main substrate 8.

<First Sealing Resin 4>

The first sealing resin 4 is an epoxy-type adhesive, having width dimensions equivalent to or less than those of the solid-state imaging element 3.

The first conductor patterns 25a, 25b are formed at end parts of the second connection terminals 11 between the main substrate 8 and the solid-state imaging element 3 as shown in FIG. 21, and second conductor patterns 25c are formed at end parts of the cavity 7, thereby preventing the first sealing resin 4 from flowing down to the outer side of the main substrate 8 as shown in FIG. 22. The second conductor patterns 25c have a different shape from the third connection terminals 17.

In the above embodiment, the resin covering the electronic components 6 is the second sealing resin 5. The resin spreading of which is prevented by the second conductor pattern 25c is the second sealing resin 5 in another embodiment.

<First Conductor Patterns 25a, 26b, Second Conductor Pattern 25c>

The first conductor patterns 25a, 25b and the second conductor pattern 25c are formed of, for example, aluminum; however, a metal such as copper having a higher conductivity than aluminum or tungsten may be used. It is also preferable that nickel/gold plating is applied to copper so as not to be oxidized easily.

The first conductor patterns 25a, 25b and the second conductor pattern 25c are preferably formed by the same process as the second connection terminals 11 and the third connection terminals 17.

The first conductor patterns 25a, 25b and the second conductor pattern 25c are also used as recognition marks for positioning in the mounter used when connecting the main substrate 8 and the solid-state imaging element 3. The first conductor patterns 25a, 25b and the second conductor patterns 25c preferably have different shapes from that of the second connection terminals 11 and the shape whereby the first sealing resin 4 does not fall down to the outer side of the main substrate 8. The first conductor patterns 25a, 25b are corner marks each having a size of 0.3 mm×0.1 mm in a longitudinal direction and 0.15 mm×0.1 mm in a short-side direction, the first conductor pattern 25b has a rectangular shape with a size of 0.1 mm×0.08 mm and the second conductor pattern 25c has a rectangular shape with a size of 0.7 mm×0.08 mm.

It is preferable that only the second conductor patterns 25c are provided without providing the first conductor patterns 25a, 25b according to Embodiment 6.

End parts around a cross section in which the solid-state imaging device exists are surrounded by the first conductor patterns 25a, 25b and the second conductor pattern 25c. The end parts are surrounded by the sealing resin.

Embodiment 8

FIG. 23, FIG. 24 are plan views of a solid-state imaging device according to Embodiment 8 of the present invention, in which FIG. 23 is a view before sealing and FIG. 24 is a view after sealing. Items not explained are the same as those of Embodiments 6, 7.

<First Sealing Resin 4>

The first sealing resin 4 is an epoxy-type adhesive, having width dimensions equivalent to or less than those of the solid-state imaging element 3.

The first conductor patterns 25a are formed at end parts of the main substrate 8 as shown in FIG. 23, thereby preventing the first sealing resin 4 from falling down to outer sides of the first conductor patterns 25a formed at end parts of the joined part as shown in FIG. 24.

As plating processing is further applied to the first conductor patterns 25a, the first sealing resin 4 wets and spreads to the end parts of the conductor patterns 25 to form a fillet.

Here, the first conductor patterns 25a are also used as recognition marks for positioning in the mounter used when connecting the main substrate 8 and the solid-state imaging element 3. A shape of the first conductor patterns 25a is a circular shape larger than the second connection terminals 11.

The first sealing resin 4 may be formed in the area of the cavity 7 as long as the first sealing resin 4 does not flow down to the outer side of the main substrate 8.

<First Conductor Pattern 25a>

The first conductor patterns 25a are formed of, for example, aluminum or the like; however, a metal such as copper having a higher conductivity than aluminum or tungsten may be used. It is also preferable that nickel/gold plating is applied to copper so as not to be oxidized easily.

The first conductor patterns 25a are also used as recognition marks for positioning in the mounter used when connecting the main substrate 8 and the solid-state imaging element 3. The first conductor patterns 25a have a circular shape larger than the second connection terminals 11 and the shape whereby the first sealing resin 4 does not fall down to the outer side of the main substrate 8. The size of the second connection terminals 11 is 0.1 mm in diameter, whereas the size of the first conductor patterns 25a is 0.2 mm in diameter.

<Advantages>

When the connection terminals are formed on the back surface of the light receiving surface as in the above structure, an occupancy in the light receiving surface of the solid-state imaging element is increased and performance and efficiency in solid-state imaging are not impaired. Moreover, the sealing resin forms the fillet extending to end parts of the main substrate without falling down to the side surface of the main substrate due to the conductor patterns formed in end parts of the connection terminals to thereby provide a small-sized solid state imaging device with high reliability and high performance.

(In Whole)

Embodiments 1 to 8 may be combined.

INDUSTRIAL APPLICABILITY

The solid-state imaging device according to the present disclosure is widely used as a small-sized solid-state imaging device. For example, it is used as a solid-state imaging device for an endoscope.

REFERENCE SIGNS LIST

1 transparent member
2 adhesive
3 solid-state imaging element
3a light receiving surface
3b through via
3c back surface
4 first sealing resin
5 second sealing resin
5a tapered part
6 electronic component
7 cavity
8 main substrate
8a protruding part
8b base part
8c first cutout part
8d second cutout part
9 first connection terminal
A dashed line
B area
C fillet
10 bump electrode
11 second connection terminal
12 joining material
13 bump electrode
14 second connection terminal
17 third connection terminal
15 connection terminal
16 connection terminal
23 joining material
25 conductor pattern
25a first conductor pattern
25b first conductor pattern
25c second conductor pattern
26 third sealing resin
32 connection terminal
w1 width
w2 width
w3 width
w4 width
101 transparent material
103 solid-state imaging element
104 sealing resin
110 bump electrode
112 lead

The invention claimed is:

1. A solid-state imaging device comprising:
   a solid-state imaging element including a light receiving surface and back surface on an opposite side to the light receiving surface;
   a main substrate connected to the back surface of the solid-state imaging element;
   electronic components mounted on the main substrate; and
   a sealing resin positioned between the solid-state imaging element and the main substrate,
   wherein
   the main substrate has a base part and a protruding part,
   the base part has a first surface facing the back surface of the solid-state imaging element,
   the protruding part protrudes from the first surface of the base part and is connected to the back surface of the solid-state imaging element,
   the electronic components are mounted on the first surface of the base part between the main substrate and the solid-state imaging element,
   an outer edge of the main substrate seen from the light receiving surface side of the solid-state imaging element is positioned within an outer edge of the solid-state imaging element, and
   an outer edge of the sealing resin seen from the light receiving surface side of the solid-state imaging element is positioned within the outer edge of the solid-state imaging element.

2. The solid-state imaging device according to claim 1, further comprising:
   a transparent member fixed to the light receiving surface of the solid-state imaging element by an adhesive,
   wherein an outer edge of the transparent member seen from the light receiving surface side of the solid-state imaging element is positioned within the outer edge of the solid-state imaging element, and
   an outer edge of the adhesive seen from the light receiving surface side of the solid-state imaging element is positioned within the outer edge of the solid-state imaging element.

3. The solid-state imaging device according to claim 1,
   wherein cavities as spaces for the electronic components being mounted are formed on the left and right of the main substrate when seen from the light receiving surface side of the solid-state imaging element.

4. A solid-state imaging device comprising:
   a solid-state imaging element including a light receiving surface and back surface on an opposite side to the light receiving surface;
   a main substrate connected to the back surface of the solid-state imaging element electronic components mounted on the main substrate; and
   a sealing resin positioned between the solid-state imaging element and the main substrate,
   wherein
   the main substrate has a base part and a protruding part,
   the base part has a first surface facing the back surface of the solid-state imaging element,
   the protruding part protrudes from the first surface of the base part and is connected to the back surface of the solid-state imaging element,
   the electronic components are mounted on the first surface of the base part between the main substrate and the solid-state imaging element,
   the sealing resin is a laminated body of a first sealing resin and a second sealing resin,
   the first sealing resin is disposed on a solid-state imaging element side and the second sealing resin is disposed on a main substrate side, and
   a boundary surface between the first sealing resin and the second sealing resin inclines so that a thickness of the first sealing resin is reduced from an inside to an outside of the solid-state imaging device.

5. The solid-state imaging device according to claim 4, wherein the first sealing resin covers connection electrodes connecting the solid-state imaging element to the main substrate.

6. The solid-state imaging device according to claim 4, wherein the second sealing resin seals the components.

7. The solid-state imaging device according to claim 4, wherein the second sealing resin has a higher heat dissipation than that of the first sealing resin.

8. The solid-state imaging device according to claim 4, wherein the second sealing resin is more flexible than the first sealing resin.

* * * * *